US011728013B2

(12) United States Patent
Boston et al.

(10) Patent No.: US 11,728,013 B2
(45) Date of Patent: Aug. 15, 2023

(54) SYSTEMS AND METHODS FOR MANAGING, STORING, AND EXCHANGING HEALTHCARE INFORMATION ACROSS HETEROGENEOUS HEALTHCARE SYSTEMS

(71) Applicant: InteliChart, LLC, Fort Mill, SC (US)

(72) Inventors: Christopher John Boston, Waxhaw, NC (US); Gary Robert Hamilton, Waxhaw, NC (US); Robert George Hamilton, Mooresville, NC (US); Charles David Myers, Matthews, NC (US); William Francis Plourde, Charlotte, NC (US); Ruben Dario Sosa, Charlotte, NC (US)

(73) Assignee: Intelichart, LLC, Fort Mill, SC (US)

( * ) Notice: Subject to any disclaimer, the term of this patent is extended or adjusted under 35 U.S.C. 154(b) by 268 days.

(21) Appl. No.: 14/333,132

(22) Filed: Jul. 16, 2014

(65) Prior Publication Data
US 2016/0019346 A1 Jan. 21, 2016

(51) Int. Cl.
*G16H 10/60* (2018.01)
(52) U.S. Cl.
CPC .................................. *G16H 10/60* (2018.01)
(58) Field of Classification Search
None
See application file for complete search history.

(56) References Cited

U.S. PATENT DOCUMENTS

| | | | |
|---|---|---|---|
| 2003/0204420 A1* | 10/2003 | Wilkes | A47B 81/00 705/3 |
| 2006/0161840 A1 | 7/2006 | Cohen et al. | |
| 2007/0016450 A1* | 1/2007 | Bhora | G16H 40/67 705/3 |
| 2009/0080408 A1* | 3/2009 | Natoli | H04L 67/565 370/351 |
| 2010/0131299 A1* | 5/2010 | Hasan | G06Q 10/00 705/3 |
| 2011/0173168 A1 | 7/2011 | Jones et al. | |
| 2014/0214450 A1 | 7/2014 | Bechtold et al. | |

* cited by examiner

*Primary Examiner* — Rachelle L Reichert
(74) *Attorney, Agent, or Firm* — Morris, Manning & Martin, LLP; Daniel E. Sineway, Esq.; Daniel T. Begasse

(57) ABSTRACT

Aspects of the present disclosure generally relate to systems and methods for accessing, managing, and exchanging patient information across a plurality of providers that may have various discrete medical record systems, including, but not limited to medical facilities, clinics, ambulatory emergency health systems, and other providers (e.g., heterogeneous healthcare providers). In various embodiments, the system receives a request from a requesting party for one or more records of a particular patient. In response, in one or more embodiments, the system identifies what information (if any) the requester is authorized to receive, retrieves the information the requester is authorized to receive from various discrete medical record systems, then normalizes and aggregates the retrieved information. In a particular embodiment, the system also denormalizes the data (e.g., converts the data to the local format and terms of the requester) before transmitting the retrieved data to the requester.

20 Claims, 10 Drawing Sheets

EXEMPLARY UMIS ENVIRONMENT

EXEMPLARY UMIS ARCHITECTURE

HIGH-LEVEL EXEMPLARY UMIS PROCESS

EXEMPLARY PERMISSIBLE SEGMENT
IDENTIFICATION PROCESS

EXEMPLARY NORMALIZATION PROCESS

EXEMPLARY DENORMALIZATION PROCESS

EXEMPLARY PATIENT INFORMATION UPDATE PROCESS

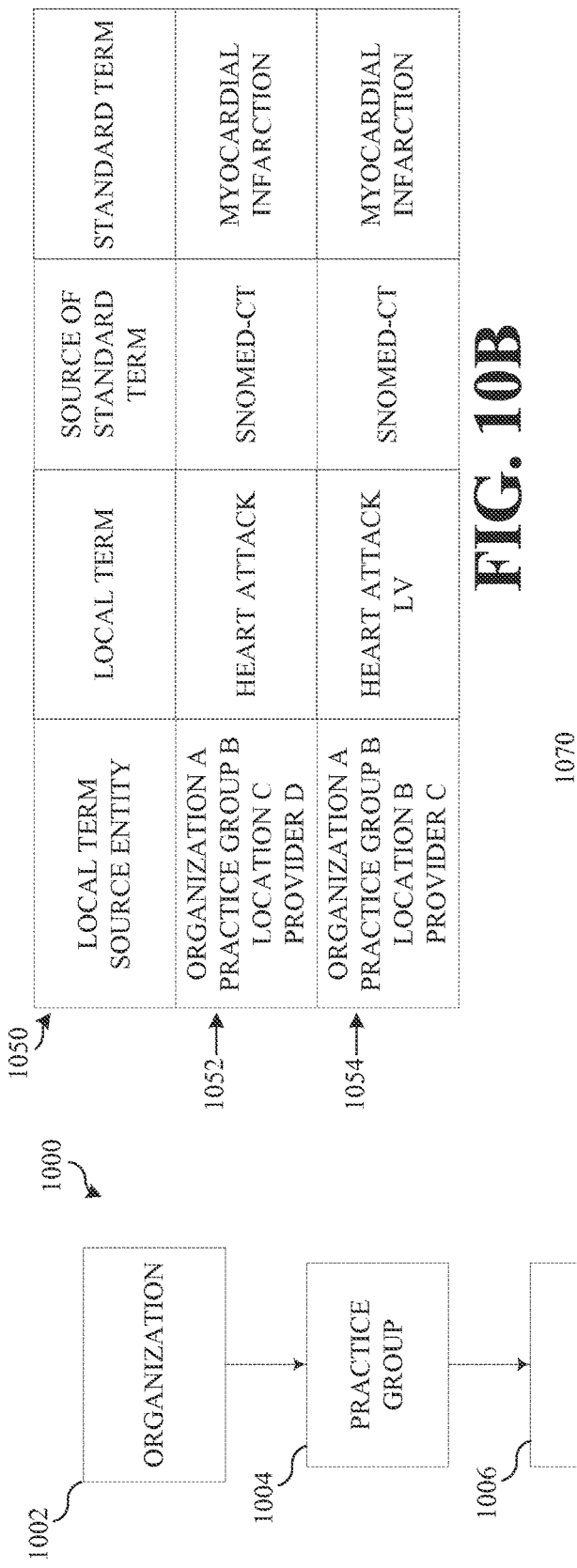

SYSTEMS AND METHODS FOR MANAGING, STORING, AND EXCHANGING HEALTHCARE INFORMATION ACROSS HETEROGENEOUS HEALTHCARE SYSTEMS

CROSS-REFERENCE TO RELATED APPLICATIONS

This application is related to pending U.S. patent application Ser. No. 14/333,179 filed Jul. 16, 2014, entitled "SYSTEMS AND METHODS FOR MANAGING, STORING, AND EXCHANGING HEALTHCARE INFORMATION ACROSS HETEROGENEOUS HEALTHCARE SYSTEMS," by Christopher John Boston et al., and pending U.S. patent application Ser. No. 14/333,215 filed Jul. 16, 2014, entitled "SYSTEMS AND METHODS FOR MANAGING, STORING, AND EXCHANGING HEALTHCARE INFORMATION ACROSS HETEROGENEOUS HEALTHCARE SYSTEMS," by Christopher John Boston et al., the disclosures of which are both hereby incorporated by reference as if set forth herein in their entireties.

TECHNICAL FIELD

The present systems and methods relate generally to healthcare informatics as well as the storage, exchange, and analysis of healthcare information. More particularly, the present systems and methods relate to management, exchange, storage, and retrieval of patient information among multiple healthcare providers and organizations across multiple platforms.

BACKGROUND

Historically, due to patient privacy customs, laws, and other considerations, each healthcare provider has kept its own medical records, data, and other patient information. Thus, many healthcare providers have developed their own systems of managing this patient data, including use of local terminology and formatting for prescriptions, diagnosis, demographic information, etc. Further, healthcare providers and organizations typically utilize discrete and local management systems that were to keep patient health information localized and siloed. In other words, because healthcare data was not shared, healthcare record systems were not designed to be shared.

Now, there is a push for healthcare data to be shared for various reasons, including larger pools for statistical data, for sharing best practices, and healthcare cost reduction. Therefore, there is a long-felt but unresolved need for a system or method that is agnostic to the various terminology and formatting of a plurality of medical facilities and providers. Further, there is a need for a system or method that allows medical providers to access and view a patient's medical information that is aggregated from the plurality of medical facilities and providers. Various embodiments of the present systems and methods recognize and address the foregoing considerations.

BRIEF SUMMARY OF THE DISCLOSURE

Briefly described, and according to one embodiment, aspects of the present disclosure generally relate to systems and methods for managing and securely storing and exchanging patient information across a plurality of medical facilities and providers.

Aspects of the present disclosure generally relate to systems and methods for accessing, managing, and exchanging patient information across a plurality of providers that may have various discrete medical record systems, including, but not limited to medical facilities, clinics, ambulatory emergency health systems, and other providers (e.g., heterogeneous healthcare providers).

In a particular embodiment, a Universal Medical Information System ("UMIS") allows various medical providers in various physical locations to securely store and exchange real-time data across discrete medical record systems. In one or more embodiments, the UMIS utilizes a substantially real-time bi-directional data exchange such that providers have the most up-to-date patient information available. Additionally, in some embodiments, the UMIS enables medical providers to exchange records and information according to their own terminology and format by normalizing, aggregating, and denormalizing data when a request for data is received. Instead of a complex mesh wherein, for example, a hospital has separate protocols and communications links in place for exchanging information with other hospitals and respective providers, who in turn have their own separate protocols and communications links in place for doing the same, the UMIS provides a streamlined, unified, universal system.

Accordingly, in one embodiment, the UMIS: 1) receives a request to present data associated with a particular patient from a requester; 2) in response to receiving the request, identifies and extracts permissible segments of information, relevant to the request, that are sharable to and viewable by the requester (e.g., based on patient preferences, privacy laws, etc.), from various providers connected to the system; 3) normalizes the extracted data (e.g., where the data from each of the various providers contains local terminology and/or local formatting) to a standardized format and to standardized terms; 4) aggregates the normalized data (e.g., compares portions of the normalized, extracted data to eliminate repeat entries); 5) denormalizes the extracted, aggregated data to a set of terms and format local to the requester; and 6) presents the data to the requester. In this way, a requester can receive, manage, and view concise, relevant patient information from various medical providers in the requester's own local terms and format.

To further the understanding of the present systems and methods, a brief discussion example is provided immediately below. In this example, assume Doctor A is seeing Patient A for the first time. Doctor A, in this example, has his own medical record system, which stores all patient medical records and demographics in a local terminology and format called Set A.

Continuing with this example, Doctor A, while preparing to see Patient A, queries the UMIS for all demographic information associated with Patient A. The system, in response to the request from Doctor A, in this example, determines that Doctor A can view and can be sent Patient A's demographic information (e.g., because Doctor A is a licensed physician, because Doctor A has the patient's permission, etc.). In this example, the system then extracts demographic information from three other providers, including the following information: 1) Patient A's birth date is 03/27/1986 from Hospital 1; 2) Patient A's birth date is Mar. 27, 1986, from Hospital 2; and 3) Patient A's birthdate is 27/03/1986 from Provider 1.

Continuing with this example, the UMIS is configured to normalize the extracted information to a predetermined standard format (e.g., a standard UMIS format), where the birthdate format is "MM/DD/YYYY." Thus, in this example, the system converts all three of the birthdays to "03/27/1986." Continuing with this example, the system then aggregates the birthdays from the three providers. Here, in this example, the system aggregates the birthdays to a single entry of "03/27/1986." It should be noted that the system, in various embodiments, is configured to indicate that each of the providers included the same birthdate (e.g., provide an indication with the single birthday entry that the birthdate was provided by Hospital 1, Hospital 2, and Provider 1).

Still continuing with this example, the system is then configured to denormalize the data for the purpose of presenting it to Doctor A in his preferred viewing format and terminology. Here, the system receives (or previously received, in various embodiments) information from Doctor A that Set A (the format and terminology system Doctor A uses) displays birthdays in a "DD/MM/YY" format. The system then translates the extracted, normalized, and aggregated birthday of "03/27/1986" to the Set A format of "27/03/86." The system then, in this example, displays the birthday to Doctor A.

In various embodiments, the UMIS may also be configured to substantially automatically update the UMIS and various third-party registries when information about a particular patient is changed. As a brief example, the UMIS may be configured to: 1) receive or retrieve changed information associated with the particular patient from a first third-party registry; 2) update the UMIS based on the changed information; and/or 3) update one or more other third-party registries based on the changed information. In the embodiment described above, the system may also identify permissible segments of the changed information and normalize, aggregate, and denormalize the changed information before updating the one or more other third-party registries.

The UMIS, in the embodiments described above, may be provided in any of a variety of ways by any appropriate entity. Additionally, the system may be implemented, at least in part, on various computing devices (laptop computer, desktop computer, mobile device, etc.), on a one or more provider's servers, on one or more third-party servers and/or or any combination thereof. The following illustrates an exemplary embodiment of the UMIS including exemplary computer architecture for the UMIS as well as a number of examples of the UMIS functionality.

According to one embodiment, a computer-implemented method for normalizing patient data includes the steps of: 1) receiving a data request, by at least one processor, from a computer system associated with a particular user, to send data associated with a particular patient to the computer system; 2) in response to receiving the data request from the computer system associated with the particular user: A) retrieving, by at least one processor, a first set of data associated with the particular patient from a computer system of a particular healthcare provider, wherein the first set of particular patient data includes one or more provider terms of the particular healthcare provider; and B) retrieving, by at least one processor, a set of local terms associated with the particular user from a database; 3) normalizing, by at least one processor, the first set of particular patient data, wherein normalizing the first set of particular patient data comprises converting at least one of the one or more provider terms to a first at least one generic term; 4) adding the normalized first set of particular patient data to a patient output record; 5) denormalizing the patient output record, wherein denormalizing the patient output record comprises converting the at least one generic term to one or more local terms of a set of local terms associated with the particular user; and 6) transmitting the denormalized patient output record to the computer system associated with the particular user.

In various embodiments, a universal medical information system for managing patient records across heterogeneous health care systems includes: 1) at least one central electronic database for storing one or more patient health records; 2) one or more registries, wherein each of the one or more registries are hosted by the universal medical archive system and comprise health record data associated with one or more patients of a third-party provider; and 3) at least one processor communicably coupled to the at least one central electronic database and the one or more registries, wherein the at least one processor is configured to: A) receive a set of local terms associated with a particular user; B) store, by at least one processor, the set of local terms in the at least one central electronic database; C) receive a data request from a computer system associated with the particular user, to send data associated with a particular patient to the computer system; D) in response to receiving the data request from the computer system associated with the particular user: i) retrieve a first set of data associated with the particular patient from a computer system of a particular healthcare provider, wherein the first set of particular patient data includes one or more provider terms of the particular healthcare provider; and ii) retrieve the set of local terms from the database; E) normalize the first set of particular patient data, wherein normalizing the first set of particular patient data comprises converting at least one of the one or more provider terms to a first at least one generic term; F) add the normalized first set of particular patient data to a patient output record comprising the first at least one generic term; G) denormalize the patient output record, wherein denormalizing the patient output record comprises converting the first at least one generic term to one or more local terms of the set of local terms; and H) transmit the denormalized patient output record to the computer system associated with the particular user.

In one or more embodiments, a universal medical information system for managing patient records across heterogeneous health care systems includes: 1) at least one central electronic database for storing one or more patient health records; 2) one or more registries, wherein each of the one or more registries are hosted by the universal medical archive system and comprise health record data associated with one or more patients of the third-party provider; and 3) at least one processor communicably coupled to the at least one central electronic database and the one or more registries, wherein the at least one processor is configured to: A) receive a data request from a computer system associated with a particular user to send data associated with a particular patient to the computer system; B) in response to receiving the data request from the computer system associated with the particular user: i) retrieve a data set associated with the particular patient from each of a plurality of computer systems of a plurality of particular healthcare providers, wherein the plurality of data sets include a plurality of provider terms; ii) determining an applicable standard for each of the plurality of data sets; and iii) converting one or more provider terms of the plurality of provider terms to one or more generic terms; C) add each of the plurality of data sets to a patient output record; D) determine whether the patient output record includes one or more duplicate generic terms; E) in response to determining that the patient output record includes one or more duplicate generic terms, modify the patient output record to exclude the one or more duplicate generic terms; F) converting each of the one or more generic terms to one or more local terms, wherein the one or more local terms are terms associated with the particular user; and G) transmit the patient output record to the computer system associated with the particular user.

In particular embodiments, a computer-implemented method for managing patient data includes the steps of: 1) receiving a request from a healthcare provider to provide particular data associated with a particular patient, wherein the request comprises a local set of rules for naming and formatting patient data; 2) in response to receiving the request from the provider, extracting a data element corresponding to the particular data from a plurality of data elements, wherein the plurality of data elements are stored in a centralized database, are formatted according to a centralized set of rules, and include a source identifier; 3) determining whether the source identifier of the extracted data element corresponds to the healthcare provider; 4) in response to determining that the source identifier of the extracted data element does not correspond to the healthcare provider, determining whether the extracted data is named and formatted according to the local set of rules; 5) in response to determining that the extracted data is not named and formatted according to the local set of rules, conforming the extracted data with the local set of rules; and 6) transmitting the conformed extracted data to the healthcare provider.

According to at least one embodiment, a computer-implemented method for updating one or more patient records includes the steps of: 1) receiving, by at least one processor, real-time patient data from a computer system associated with a first vendor, wherein the patient data includes: A) information associated with a particular patient; and B) a first vendor identifier; 2) determining whether the received patent data is included in an existing patient health record database; 3) in response to determining the received patient data is not included in the existing patient health record database, adding, by at least one processor, the received patent data to the existing health record database; 4) in response to receiving the received patient data, locating, by at least one processor, one or more third-party patient registries that include health record data associated with the particular patient; 5) in response to locating the one or more third-party patient registries that include health record data associated with the particular patient, determining whether the one or more third party patient registries include the received patient data; 6) in response to determining the one or more third party patient registries include the received patient data, determining whether the received patient data included in the one or more third-party registries originated from the first vendor based at least in part on the first vendor identifier; and 7) in response to determining the received patient data included in the one or more third-party registries did not originate from the first vendor, modifying, by at least one processor, the received patient data included in the one or more third-party patient registries to include the first vendor identifier.

In further embodiments, a universal medical information system for updating patient records across heterogeneous health care systems includes: 1) at least one central electronic database for storing one or more patient health records; 2) one or more registries hosted by the universal medical information system and comprising health record data associated with one or more patients of the third-party provider; and 3) at least one processor communicably coupled to the at least one central electronic database and the one or more registries, wherein the at least one processor is configured to: A) receive real-time patient data from a first registry of the one or more registries, wherein the patient data comprises: i) first patient information associated with a particular patient; and ii) a first provider identifier indicating a provider that is associated with the first patient information; B) determine whether the received patient data exists in the at least one central electronic database; C) in response to determining that the received patient data does not exist in the at least one central electronic database, modify the at least one at least one central electronic database to include the received patient data; D) locate at least one of the one or more registries that include health record data associated with the particular patient; E) in response to locating the at least one registry, determining whether the at least one registry includes the received patient data; F) in response to determining the at least one registry includes the received patient data, determining whether the received patient data included in the at least one registry originated from the first registry based at least in part on the first provider identifier; and G) in response to determining the received patient data included in the at least one registry did not originate from the first registry, modifying the received patient data included in the at least one registry to include the first provider identifier.

In still further embodiments, a computer system including at least one processor is configured to: 1) receive real-time patient data from a first registry of one or more registries, wherein the patient data includes: A) one or more segments of information associated with a particular patient; and B) a first provider identifier, wherein the first provider identifier is an indicator of the identity of the provider that provided with the one or more segments; 2) determine whether each of the one or more segments exists in a central database associated with the at least one processor; 3) in response to determining that at least one segment of the one or more segments does not exist in the central database, adding the at least one segment to the central database; 4) in response to determining that the at least one segment exists in the central database, determine whether the existing at least one segment is associated with the first provider identifier; 5) in response to determining that the existing at least one segment is not associated with the first provider identifier, associating the existing at least one segment with the first provider identifier; 6) locate at least one of the one or more registries that include health record data associated with the particular patient; 7) in response to locating the at least one registry, determining whether the at least one registry includes the at least one segment; 8) in response to determining the at least one registry includes the at least one segment, determining whether at least one segment included in the at least one registry originated from the first registry based at least in part on the first provider identifier; and 9) in response to determining the at least one segment included in the at least one registry did not originate from the first registry, modify the at least one segment included in the at least one registry to include the first provider identifier.

According particular embodiments, a computer-implemented method for exchanging information across varying medical record systems includes the steps of: 1) receiving a request, by at least one processor, from a requester, to view data associated with a particular patient; 2) in response to receiving the request, retrieving, by at least one processor: A) a first segment of data associated with the particular patient, wherein: i) the first segment comprises one or more data elements; and ii) the first segment is retrieved from a first record system of a plurality of record systems; and B) a second segment of data associated with the particular patient, wherein: i) the second segment comprises one or more data elements; and ii) the second segment is retrieved from a second record system of the plurality of record systems; 3) extracting, by at least one processor: A) a first data element from the one or more data elements of the first segment; and B) a second data element from the one or more data elements of the second segment; 4) determining, by at least one processor, whether an equivalent to the first data element is included in a results set, wherein the results set includes the data to be displayed to the requester; 5) in response to determining that the equivalent to the first data element is not included in the results set, adding the first data element to the results set; 6) determining whether an equivalent to the second data element is included in the results set; 7) in response to determining that the equivalent to the second data element is not included in the results set, adding the second data element to the results set; 8) determining, by at least one processor, whether all data segments associated with the particular patient have been extracted; and 9) in response to determining that all data segments associated with the particular patient have been extracted, displaying the results set to the requester, whereby, the results set, as displayed, includes one or more elements associated with the particular patient formatted according to local formatting rules associated with the requester.

In one or more embodiments, a universal medical information system for updating patient records across heterogeneous health care systems includes: 1) at least one central electronic database for storing one or more patient health records; 2) one or more registries, wherein each of the one or more registries are one or more databases hosted by the universal medical information system and comprise health record data associated with one or more patients of one or more third-party providers; and 3) at least one processor communicably coupled to the at least one central electronic database and the one or more registries, wherein the at least one processor is configured to: A) receive a request, from a requester, to view data associated with a particular patient; in response to receiving the request, retrieve: i) a first segment of data associated with the particular patient, wherein: a) the first segment comprises one or more data elements; and b) the first segment is from a first registry of the one or more registries; and ii) a second segment of data associated with the particular patient, wherein: a) the second segment comprises one or more data elements; and b) the second segment is from a second registry of the one or more registries; B) extract: i) a first data element from the one or more data elements of the first segment; and ii) a second data element from the one or more data elements of the second segment; C) determine whether an equivalent to the first data element is included in a results set, wherein the results set includes the data to be displayed to the requester; D) in response to determining that the equivalent to the first data element is not included in the results set, add the first data element to the results set; E) determine whether an equivalent to the second data element is included in the results set; F) in response to determining that the equivalent to second data element is not included in the results set, add the second data element to the results set; G) determine whether all data segments associated with the particular patient have been extracted; and H) in response to determining that all data segments associated with the particular patient have been extracted, display the results set to the requester, whereby: i) the results set, as displayed, includes one or more elements associated with the particular patient formatted according to local formatting rules associated with the requester; and ii) the local formatting rules are stored by the central electronic database.

In a particular embodiment, a system for updating records across heterogeneous systems includes: 1) at least one central electronic database for storing one or more records; 2) one or more registries, wherein each of the one or more registries are one or more databases hosted by the system and comprise record data associated with one or more entities associated with one or more third-party providers; and 3) at least one processor communicably coupled to the at least one central electronic database and the one or more registries, wherein the at least one processor is configured to: A) receive a request, from a requester, to view data associated with a particular entity; B) in response to receiving the request, retrieve: i) a first segment of data associated with the particular entity, wherein: a) the first segment comprises one or more data elements; and b) the first segment is from a first registry of the one or more registries; and ii) a second segment of data associated with the particular entity, wherein: a) the second segment comprises one or more data elements; and b) the second segment is from a second registry of the one or more registries; C) extract: i) a first data element from the one or more data elements of the first segment; and ii) a second data element from the one or more data elements of the second segment, wherein the first data element and the second data element each comprise a similar type of data; D) determine whether the first data element and the second data element are included in a results set, wherein the results set includes the data to be displayed to the requester; E) in response to determining that the first and second data elements are not included in the results set, determining whether the results set is configured for two data elements of the similar type of data; F) in response to determining that the results set is not configured for two data element of the similar type of data, determining whether the first data element is more recent than the second data element; G) in response to determining that the first element is more recent than the second data element: i) discard the second data element; and ii) add the first data element to the results set; H) display the results set to the requester, whereby: i) the results set, as displayed, includes one or more elements associated with the particular entity formatted according to local formatting rules associated with the requester; and ii) the local formatting rules are stored by the central electronic database.

These and other aspects, features, and benefits of the claimed invention(s) will become apparent from the following detailed written description of the various embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein:

FIG. 10A depicts an exemplary hierarchical determination of terminology for a provider according to a particular embodiment.

FIG. 10B depicts a chart showing exemplary local source term entities, exemplary local terms, exemplary sources of standard terms, and exemplary standard terms according to a particular embodiment.

FIG. 10C shows a table with examples of various domains (e.g., categories) and exemplary corresponding applicable standards.

DETAILED DESCRIPTION

Figure 1:
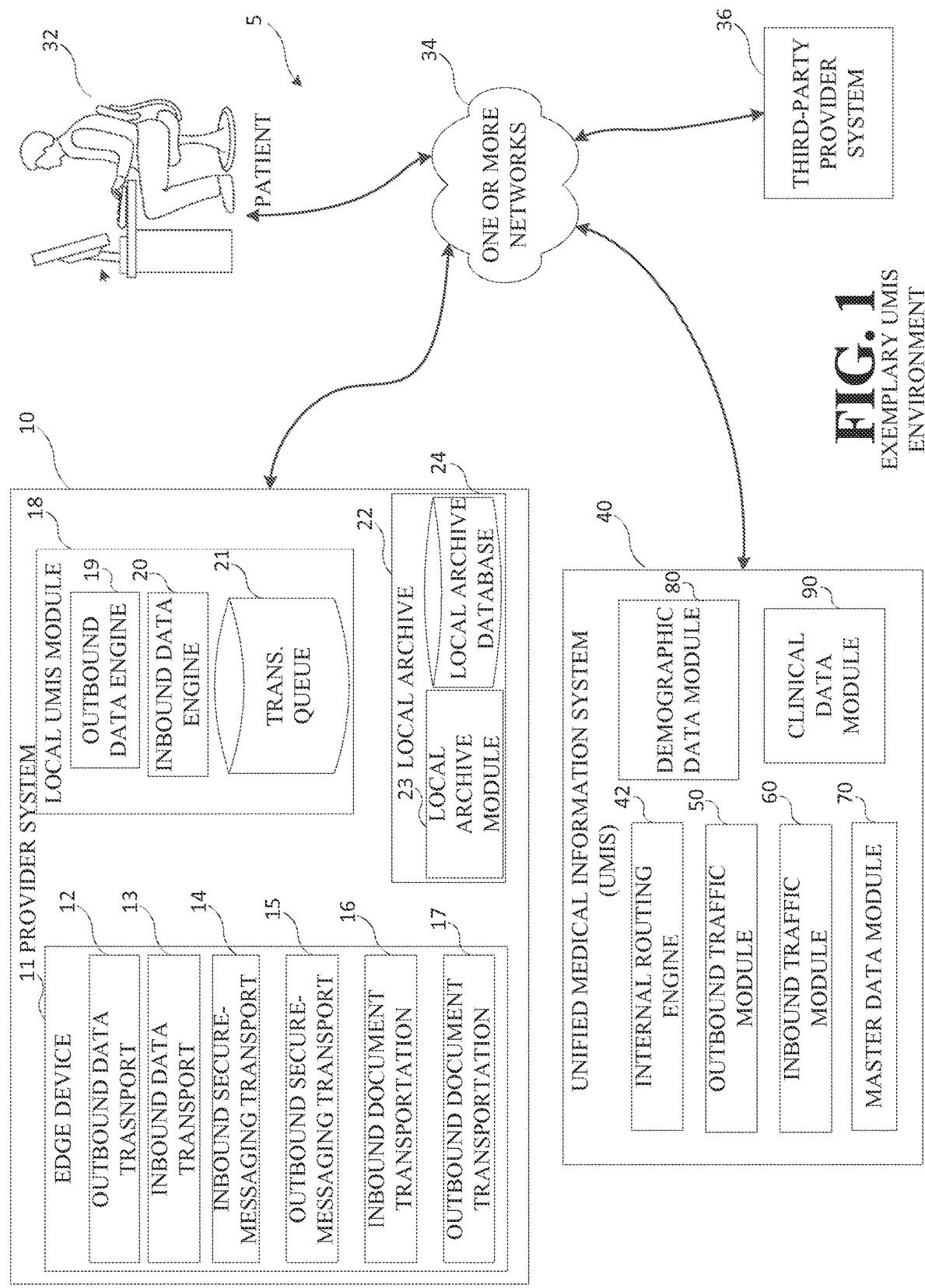
FIG. 1 is an exemplary environment in which an embodiment of the disclosed Universal Medical Information System ("UMIS") may be utilized.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments and any further applications of the principles of the disclosure as illustrated therein are contemplated as would normally occur to one skilled in the art to which the disclosure relates.

Overview

Aspects of the present disclosure generally relate to systems and methods for accessing, managing, and exchanging patient information across a plurality of providers that may have various discrete medical record systems, including, but not limited to medical facilities, clinics, ambulatory emergency health systems, and other providers (e.g., heterogeneous healthcare providers).

In a particular embodiment, a Universal Medical Information System ("UMIS") allows various medical providers in various physical locations to securely store and exchange real-time data across discrete medical record systems. In one or more embodiments, the UMIS utilizes a substantially real-time bi-directional data exchange such that providers have the most up-to-date patient information available. Additionally, in some embodiments, the UMIS enables medical providers to exchange records and information according to their own terminology and format by normalizing, aggregating, and denormalizing data when a request for data is received. Instead of a complex mesh wherein, for example, a hospital has separate protocols and communications links in place for exchanging information with other hospitals and respective providers, who in turn have their own separate protocols and communications links in place for doing the same, the UMIS provides a streamlined, unified, universal system.

Accordingly, in one embodiment, the UMIS: 1) receives a request to present data associated with a particular patient from a requester; 2) in response to receiving the request, identifies and extracts permissible segments of information, relevant to the request, that are sharable to and viewable by the requester (e.g., based on patient preferences, privacy laws, etc.), from various providers connected to the system; 3) normalizes the extracted data (e.g., where the data from each of the various providers contains local terminology and/or local formatting) to a standardized format and to standardized terms; 4) aggregates the normalized data (e.g., compares portions of the normalized, extracted data to eliminate repeat entries); 5) denormalizes the extracted, aggregated data to a set of terms and format local to the requester; and 6) presents the data to the requester. In this way, a requester can receive, manage, and view concise, relevant patient information from various medical providers in the requester's own local terms and format.

To further the understanding of the present systems and methods, a brief discussion example is provided immediately below. In this example, assume Doctor A is seeing Patient A for the first time. Doctor A, in this example, has his own medical record system, which stores all patient medical records and demographics in a local terminology and format called Set A.

Continuing with this example, Doctor A, while preparing to see Patient A, queries the UMIS for all demographic information associated with Patient A. The system, in response to the request from Doctor A, in this example, determines that Doctor A can view and can be sent Patient A's demographic information (e.g., because Doctor A is a licensed physician, because Doctor A has the patient's permission, etc.). In this example, the system then extracts demographic information from three other providers, including the following information: 1) Patient A's birth date is 03/27/1986 from Hospital 1; 2) Patient A's birth date is Mar. 27, 1986, from Hospital 2; and 3) Patient A's birthdate is 27/03/1986 from Provider 1.

Continuing with this example, the UMIS is configured to normalize the extracted information to a predetermined standard format (e.g., a standard UMIS format), where the birthdate format is "MM/DD/YYYY." Thus, in this example, the system converts all three of the birthdays to "03/27/1986." Continuing with this example, the system then aggregates the birthdays from the three providers. Here, in this example, the system aggregates the birthdays to a single entry of "03/27/1986." It should be noted that the system, in various embodiments, is configured to indicate that each of the providers included the same birthdate (e.g., provide an indication with the single birthday entry that the birthdate was provided by Hospital 1, Hospital 2, and Provider 1).

Still continuing with this example, the system is then configured to denormalize the data for the purpose of presenting it to Doctor A in his preferred viewing format and terminology. Here, the system receives (or previously received, in various embodiments) information from Doctor A that Set A (the format and terminology system Doctor A uses) displays birthdays in a "DD/MM/YY" format. The system then translates the extracted, normalized, and aggregated birthday of "03/27/1986" to the Set A format of "27/03/86." The system then, in this example, displays the birthday to Doctor A.

In various embodiments, the UMIS may also be configured to substantially automatically update the UMIS and various third-party registries when information about a particular patient is changed. As a brief example, the UMIS may be configured to: 1) receive or retrieve changed information associated with the particular patient from a first third-party registry; 2) update the UMIS based on the changed information; and/or 3) update one or more other third-party registries based on the changed information. In the embodiment described above, the system may also identify permissible segments of the changed information and normalize, aggregate, and denormalize the changed information before updating the one or more other third-party registries.

The UMIS, in the embodiments described above, may be provided in any of a variety of ways by any appropriate entity. Additionally, the system may be implemented, at least in part, on various computing devices (laptop computer, desktop computer, mobile device, etc.), on a one or more provider's servers, on one or more third-party servers and/or or any combination thereof. The following illustrates an exemplary embodiment of the UMIS including exemplary computer architecture for the UMIS as well as a number of examples of the UMIS functionality.

Exemplary Embodiment

Exemplary System Architecture

Referring now to the figures, FIG. 1 is an exemplary environment 5 in which an embodiment of the disclosed Universal Medical Information System ("UMIS") 40 is utilized, constructed, and operated in accordance with various aspects of the present disclosure. As shown in FIG. 1, the exemplary environment 5 includes a provider system 10 (e.g., a healthcare provider operatively connected to a local UMIS module, such as a clinic, a family physician, an ambulatory healthcare system, a hospital, a specialist, a nursing home, a long-term care facility, etc.), an exemplary patient 32 (e.g., any suitable patient of the provider, a representative and/or caretaker of a patient, etc.), one or more networks 34, a third-party provider 36 (e.g., any of the providers listed above (or other providers) that are not operatively connected to a local UMIS module (e.g., local UMIS module 18), and the UMIS 40. In light of this disclosure, it should be understood that the exemplary environment 5 may include any number of suitable entities, including more than one provider, more than one patient, more than one third-party provider, one or more other servers, processors, networks, and/or other computing hardware and software.

According to FIG. 1, a provider system 10, in various embodiments, represents the existing system of a healthcare provider (e.g., an existing medical record system) that includes a local UMIS module 18. The provider system 10 of FIG. 1 includes an edge device 11, a local UMIS module 18, and a local archive 22, all of which may be part of the same computing device (e.g., connected via a suitable bus) and/or operatively connected by any suitable external information exchange mechanism, including, but not limited to, one or more networks, such as a local area network ("LAN") and/or a wide area network ("WAN"). It should be noted that the local UMIS module 18, in various embodiments, is physically located (e.g., installed) on the provider system 10. In some embodiments, the local UMIS module 18 is located physically remotely from the provider system 10 (e.g., accessible via the Internet, through the cloud, etc.), but runs and/or executes functions behind the provider's firewall(s).

The edge device 11 may comprise any suitable edge device that provides an entry point to the provider system 10 and/or local network. According to one embodiment, the edge device 11 manages the connectivity, communication, and exchange of information between the provider system 10, the UMIS 40, the exemplary patient 32, and/or the third-provider 36, via the one or more networks 34. The edge device 11 may comprise a general purpose computer, network attached component device, or other specific computing device or server and may be generally identified with several attributes, such as, for example, a device identifier, a device type, a network address, a location, etc.

In the embodiment shown, the edge device 11 includes several software modules and/or computer components capable of handling the various operations of the edge device 11. As shown, the edge device 11 includes an outbound data transport 12, an inbound data transport 13, an inbound secure-messaging transport 14, an outbound secure-messaging transport 15, inbound document transportation 16, and outbound document transportation 17. The outbound data transport 12, in various embodiments, transmits data from the edge device 11 to the various other components of the exemplary environment 5 via the one or more networks 34. The inbound data transport 13, in one or more embodiments, transports data from the one or more networks 34 to the other various components of the provider system 10. The inbound secure-messaging transport 14 and outbound secure-messaging transport 15, in various embodiments, use one or more security methods to securely transport messages (e.g., secure transmission of messages from the UMIS to one or more providers over an SSL connection). It should be understood, in light of this disclosure, that the system may use any suitable mechanism for the secure transmission and reception of messages, data, and documents, including encryption methods.

The inbound document transportation 16 and the outbound document transportation 17, in a particular embodiment, facilitate the transmission of one or more documents from the provider system 10 to one or more of the other various components of the exemplary environment 5 and to the provider system 10 from one or more of the other components (and/or components of one or more other systems) of the exemplary environment 5, respectively. Modules shown are for exemplary purposes only; the edge device 11 may comprise any number of suitable modules, which may function together or separately to enable the functionality described herein.

The edge device 11 is communicably connected to the local UMIS module 18. In various embodiments, the local UMIS module 18 is a module hosted by the UMIS that communicates and transfers data (e.g., patient health record data) to the provider system 10 from the UMIS 40 and from the UMIS 40 to the provider system 10 (e.g., via the edge device 11). In the embodiment shown, the local UMIS module 18 includes an outbound engine 19, an inbound engine 20, and a transmission queue 21. The outbound engine 19 and the inbound engine 20 facilitate the transmission of data relating to changes to a patient's health record (e.g., events) from the UMIS 40 and to the UMIS 40, respectively. The transmission queue 21 queues each event (e.g., each change in one or more patient's health records) change for transmission to and from the UMIS 40.

In a particular example, assume the provider system 10 (e.g., a particular patient's regular doctor) makes a change to the particular patient's health record by changing the particular patient's prescription from a 200 milligram dose of a particular medication to a 250 milligram dose of the particular medication. Continuing with this particular example, the change in the particular patient's medication triggers an event in the local UMIS module 18. Still continuing with this particular example, the event or an indication of the event (e.g., the change in dosage) may first be queued in the transmission queue 21 and then transmitted by the outbound engine 19 to the UMIS 40 via the edge device 11 and the one or more networks 34.

The local UMIS module 18 may be installed on and/or operated in connection with any suitable computing device associated with the provider system 10, such as a local computer, a local server, etc. In one or more embodiments, as will be understood by one of skill in the art, the functions of the local UMIS module 18 are carried out by one or more processors associated with the provider system 10.

The local UMIS module 18, in the embodiment shown, is communicably connected to the local archive 22, which, in various embodiments, archives health records of patents associated with the provider system 10. In various embodiments, the local archive 22 includes a local archive module 23 (e.g., that facilitates the storage of the health records of the provider system 10) and a local archive database 24 (e.g., a database that stores the health records of the provider system 10).

Still referring to FIG. 1, the provider system 10 is operatively connected to the patient 32 (e.g., via the patient's computing device), the third party-provider 36, and the UMIS 40 via the one or more networks 34, which may include any of a variety of types of computer networks such as the Internet, a private intranet, a public switch telephone network ("PSTN"), WAN, LAN, or any other type of suitable network. In certain variations of the embodiment shown, the communication link between the various components of the exemplary environment 5 are implemented via the Internet using Internet Protocol ("IP"). It should be understood that the various components of the exemplary environment 5 do not necessarily need to be deployed over the network. For example, in various embodiments, any or all of the various components associated with the patient 32, the third-party provider 36, and the UMIS 40 may be deployed locally (e.g., on a single computing device or one or more devices).

The exemplary patient 32 may, in various embodiments, represent a computer system (e.g., a laptop computer, a desktop computer, a mobile computing device, etc.) associated with one or more patients and operatively connected to the one or more networks 34. It should be noted that the system may provide the exemplary patient 32 with a unified logging system—the system enables the exemplary patient 32 (and/or the provider system 10, third-party provider 36) to log into the UMIS to view, update, and change medical records of various providers via a single log-in. The single log-in, through the UMIS, may enable the exemplary patient 32 to access, view, and/or modify his or her medical records across heterogeneous medical systems (e.g., various hospitals, providers, etc.).

The third-party provider system 36 may be any provider that is not operatively connected to a local UMIS module (e.g., local UMIS module 18). The third-party provider system 36 may be, for example, a doctor's office, hospital provider, etc. that does not have access to the UMIS 40 system because it does not have a local UMIS module installed (e.g., local UMIS module 18).

The UMIS 40 generally, in various embodiments, manages, stores, updates, normalizes, aggregates, and transmits one or more health records and related patient information (e.g., demographic information) amongst and between the various systems in the environment 5. The UMIS 40, in the embodiment shown, includes an internal routing engine 42, an outbound traffic module 50, an inbound traffic module 60, a master data module 70, a demographic data module 80, and a clinical data module 90. It should be understood, in light of this disclosure, that the modules shown are for exemplary purposes and the UMIS 40 may comprise any number of suitable modules to accomplish the functionality described herein. More specific details of the UMIS 40 are shown in FIG. 2.

Figure 2:
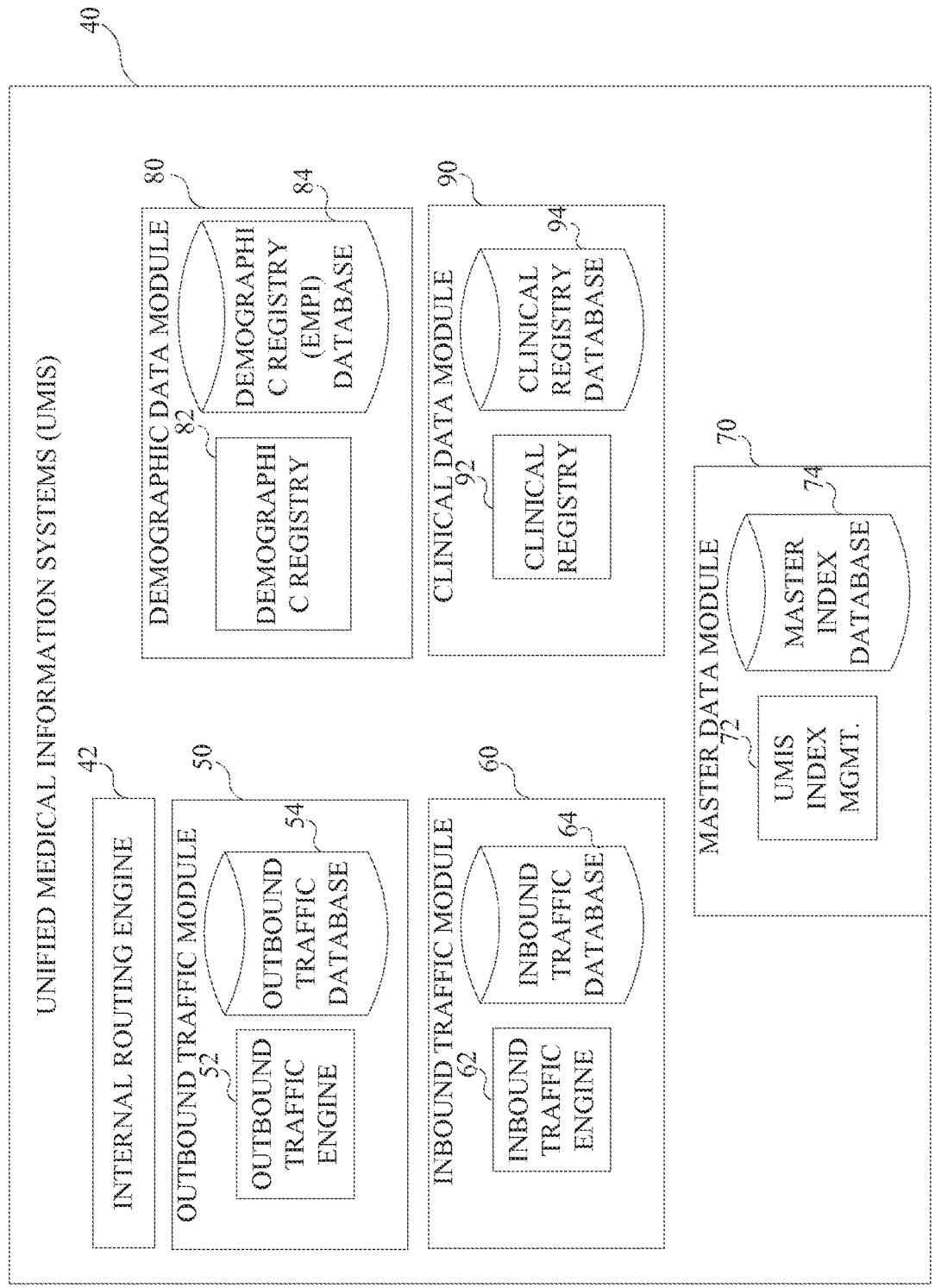
FIG. 2 is an exemplary system architecture of one embodiment of the UMIS of FIG. 1.

FIG. 2 generally shows the details of the various components of the UMIS 40, including the various modules which may along or together perform the various functions of the UMIS 40, as described herein. The internal routing engine 42 facilitates communication between the internal components of the UMIS (e.g., the outbound traffic module 50, the inbound traffic module 60, the master data module 70, the demographics data module 80, and the clinical data module 90). In various embodiments, the internal routing engine 42 determines the pathways of communication between the various components of the UMIS.

The outbound traffic module 50 generally facilitates transmitting information (e.g., data relating to changes to one or more patient health records and related data, such as demographic data) from the UMIS 40 to one or more of the other components of the exemplary environment 5 (and/or other components not shown). In the embodiment shown in FIG. 2, the outbound traffic module 50 includes an outbound traffic engine 52 that, in one or more embodiments, facilitates the transmission of information and an outbound traffic database 54 that, in a particular embodiment, stores the various transmissions by the outbound traffic engine 52.

The outbound traffic module 50 is communicably coupled to the inbound traffic module 60, which generally facilitates receiving information (e.g., receiving data relating to changes to one or more patient health records and related data, such as demographic data, from, for example, the local UMIS module 18). In various embodiments, the inbound traffic module 60 includes an inbound traffic engine 62 that, in one or more embodiments, facilitates receiving of information and an inbound traffic database 64, which, in a particular embodiment, stores the various inbound transmissions received by the inbound traffic module 60.

The master data module 70, in various embodiments, manages data within the UMIS and includes a UMIS index management engine 72 and a master index database 74. The UMIS index management engine 72 manages and indexes substantially all data in the UMIS and stores the indexed data in the master index database 74. In various embodiments, such data includes patient data, such as demographic information, prescription information, risk factors, etc. In a particular embodiment, the master index database 74 comprises information associated with a patient such that a patient can be quickly identified (e.g., a number associated with a particular patient, a code associated with the particular patient, etc.). It should be understood that the master data module 70 is configured, in many embodiments, such that it is generally secure to protect sensitive and confidential patient information.

Still referring to FIG. 2, the demographic data module 80, according to one or more embodiments, houses and manages one or more patients' demographic information, such as age, weight, sex, etc. According to particular embodiments, the demographic data module 80 includes a demographic registry 82, which manages the one or more patients' demographic information and a demographic registry database 84, which stores the one or more patients' demographic information.

The clinical data module 90, in various embodiments, manages the one or more patients' clinical information. The clinical data module 90 includes a clinical registry that manages the one or more patients' clinical data and a clinical registry database that stores the one or more patients' clinical data. It should be noted that in the embodiment shown, the demographic data module 80 and the clinical data module 90 are maintained separately for enhanced security of the one or more patients' personal health information. In other embodiments, however, the demographic data module 80 and the clinical data module 90 are managed together as a unified module/system. It should be understood that the demographic data module 80 and the clinical data module 90 are configured such that they are generally secure to patient sensitive and confidential information.

Such program modules, as displayed in FIGS. 1 and 2, are merely exemplary and may represent a number of program modules which control certain aspects of the operation of the UMIS. The modules described above may represent many modules, which may be arrange and/or with functions divided differently than depicted. Additionally, the operations and functions described could all be maintained as a single module. Exemplary embodiments of the functionality of the various modules (and other modules) are described in more detail below.

Exemplary Functionality of the System

Certain embodiments of functionality of the UMIS are shown FIGS. 3-9. The various modules depicted in FIGS. 1 and 2 may alone, or in combination, perform the steps and/or processes of FIGS. 3-9. It should be understood by reference to this disclosure that these systems and methods describe exemplary embodiments of the steps carried out by the present system, and that other exemplary embodiments may be created by adding other steps or by removing one or more of the steps shown in FIGS. 3-9.

Exemplary Process Overview

Figure 3:
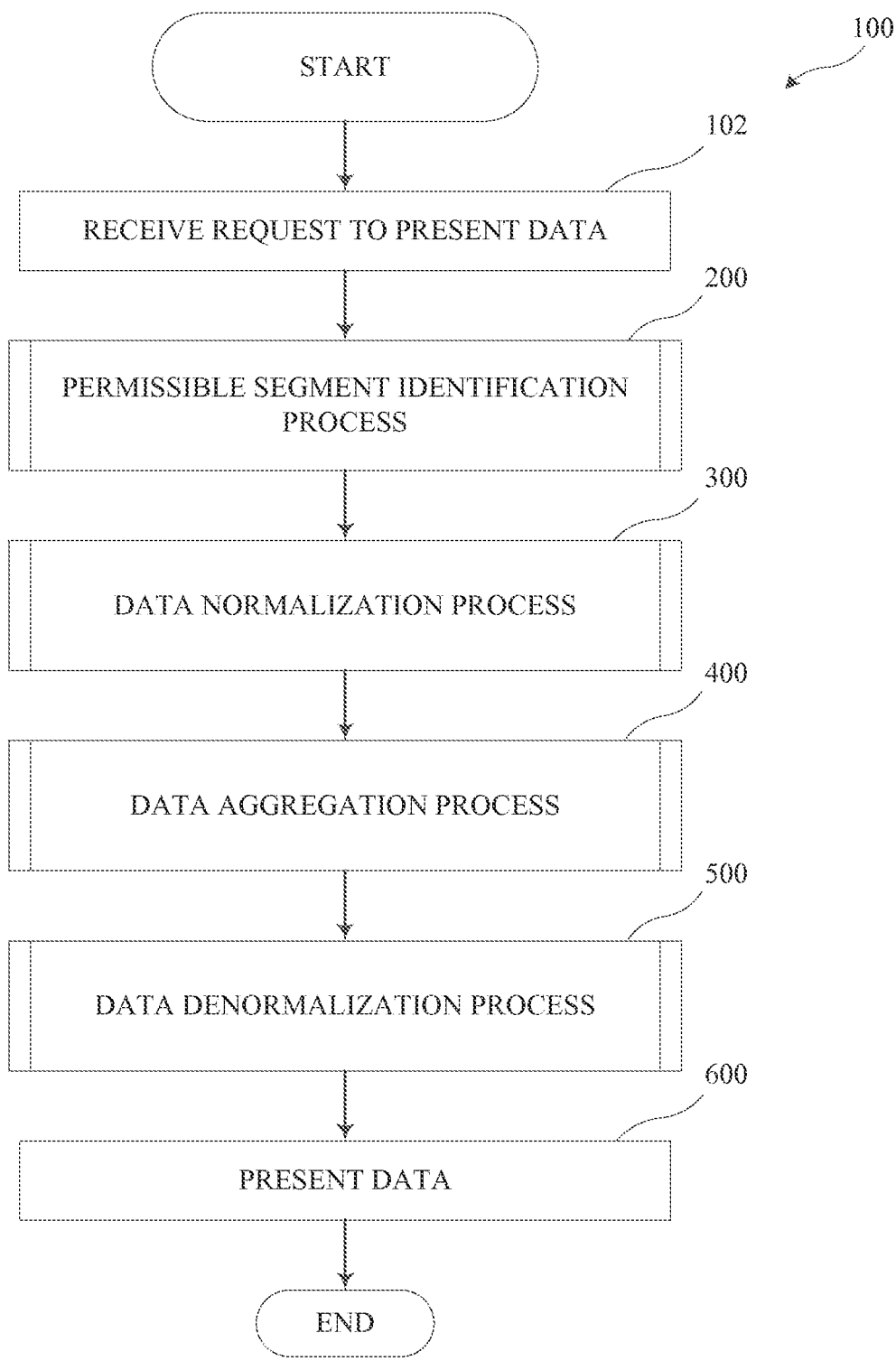
FIG. 3 is a flow chart illustrating an exemplary UMIS process executed by one or more of the modules of the exemplary system architecture of FIG. 2, according to one embodiment of the present disclosure.

FIG. 3 depicts an exemplary high-level UMIS process 100. In one embodiment, the process 300 enables presenting data (e.g., a patient health record) in response to receiving a request to view the data as executed by one or more of the modules of FIGS. 1 and/or 2, according to particular embodiments. FIGS. 4-7 depict various aspects of the process of FIG. 3 in more detail.

Turning to FIG. 3, the UMIS begins, at step 102, by receiving a request from a requester to present data. In various embodiments, the system is configured to receive the request to present the data from any suitable source, including, but not limited to, a computer system associated with a provider (e.g., the provider system 10 or the third-party provider 36) and/or a patient (e.g., the patient 32).

The system, in a particular embodiment, is configured to receive the request to present the data by the inbound traffic engine 62 via the one or more networks 34. It should be understood, in one or more embodiments, that the system may be configured to receive the request in any suitable way, including, by another suitable module and/or device (such as an edge device that is part of the UMIS).

In various embodiments, the system may be configured to receive the request via a form from a patient portal. The patient portal may be, for example, an online application that enables a patient to interact and/or communicate with healthcare providers. In one or more embodiments, the patient portal enables a patient to fill out a form to request data and/or information from the UMIS 40. The system may be configured to receive the request in any other suitable way, such as, for example, In one or more embodiments, the system is configured to receive the request via a provider request to view a patient's most up-to-date medical records (e.g., before a patient undergoes emergency surgery).

The requested data may be a request for any suitable data. In various embodiments, the requested data comprises a patient's entire medical history (e.g., an aggregation of all available data from various medical records provided by various hospitals, clinics, providers, etc.). In further embodiments, the requested data is for a specific portion of a patient's medical information, such as one or more current prescriptions, one or more known allergies of the patient, demographic information associated with the patient, etc.

In various embodiments, the request may include information additional to (or other than) a request to present data. In various embodiments, the request includes a set of one or more terms from the requester (e.g., a set of medical terms used by the requestor that the system may use to denormalize the data to local medical terms used by the requester). In one or more embodiments, the request includes various other requests, such as, for example, a time frame for presenting the data (e.g., immediately, in two days, in a number of minutes, in a number of hours, on a specific date, etc.), specific parameters to narrow the data requested (e.g., a range of data based on events, calendar dates, etc.), credentials of the requester (e.g., so the system can determine which data can be presented to the requester, based on, for example, privacy laws, patient standards, etc.), etc.

In a particular example, the request is received by the system from a computer system of a particular provider. In this particular example, assume the request is a request for current medications prescribed to a particular patient. This particular example will be used below to illustrate various exemplary functionality of the UMIS 40 throughout the following discussion of the high-level UMIS process.

At process 200, the system identifies permissible segments. According to certain aspects of the present systems and methods, one or more requesters may not be permitted to view one or more portions of patient data (e.g., because of privacy laws, patient preferences, etc.). As such, in various embodiments, permissible segments are determined portions of data viewable by the requester (e.g., determined by what data the requester is permitted to view).

In general, in one or more embodiments, the system is configured to retrieve one or more segments of data from various providers and determine which (if any) of the one or more segments of data are sharable to and viewable by this requester (e.g., the requester at step 102) based on laws, patient privacy settings, requester credentials, etc. The segments of the patient data, in general, may be various different types of data, such as for example, the patient's name, birthday, social security number, one or more prescriptions, one or more diagnoses, one or more appointment schedules, etc. The system, according to various embodiments, compiles the one or more segments that are sharable to and viewable by the requester in a permissible set, which is then normalized, aggregated, denormalized, and displayed to the requester, as further discussed below.

Figure 4:
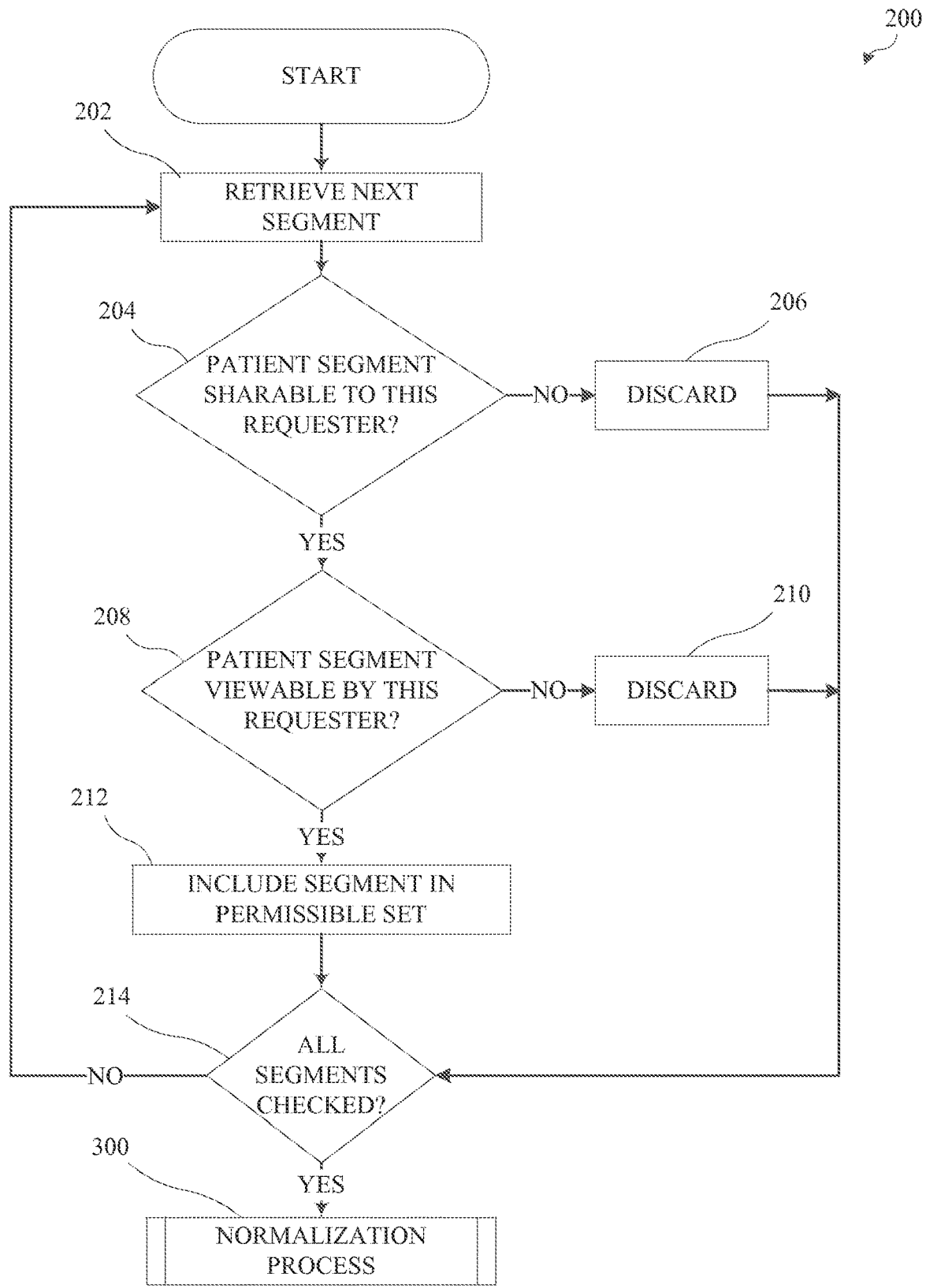
FIG. 4 is a flow chart further illustrating detailed steps of an exemplary permissible segment identification process of FIG. 3 executed by one or more of the modules of the exemplary system architecture, according to one embodiment of the present disclosure.

Continuing with the particular example from process 100, the system, at process 200, identifies two permissible segments viewable by the requester. In this particular example, the system has permission to share with and the requester has permission to view active prescriptions for the particular patient of "400 mg of ibuprofen" from Provider 1 and for "ibuprofen 400 mg" from Provider 2. The system, in this particular example, compiles "400 mg of ibuprofen" from Provider 1 and "ibuprofen 400 mg" from Provider 2 into a permissible set to be displayed to the requester. FIG. 4 further depicts an exemplary embodiment in which the system identifies permissible segments, which is discussed in detail below.

Continuing with the data normalization process 300, the system normalizes the data in the permissible set (e.g., the permissible set of identified segments above). In general, in various embodiments, the system is configured to "normalize" the permissible set by converting one or more terms of the permissible segments of the permissible set to a standard set of terms in order to facilitate a comparison of the one or more terms from various providers. The standard set of terms may be, in various embodiments, a predetermined set of terms that the UMIS uses to convert any local inbound terms to a standard set of terms.

Continuing with the above particular example, the permissible set includes two prescriptions, one for "400 mg of ibuprofen" from Provider 1 and one for "ibuprofen 400 mg" from Provider 2. In this particular example, based on a predetermined set of standard terms, the system is configured to normalize these two prescriptions to the standard format "dosage prescription." Thus, in this particular example, the system is configured to normalize each of the two prescriptions to "400 mg ibuprofen." FIG. 5 further depicts an exemplary embodiment of the normalization process 300, which is discussed in detail below.

Continuing with the discussion of FIG. 3, at process 400, the system aggregates the normalized data in the permissible set. In general, in one or more embodiments, the system is configured to check the data elements of the permissible set to combine and/or discard repeat data elements (e.g., aggregate the data). In this way, the system substantially eliminates repetitive data of the permissible set.

Figure 6:
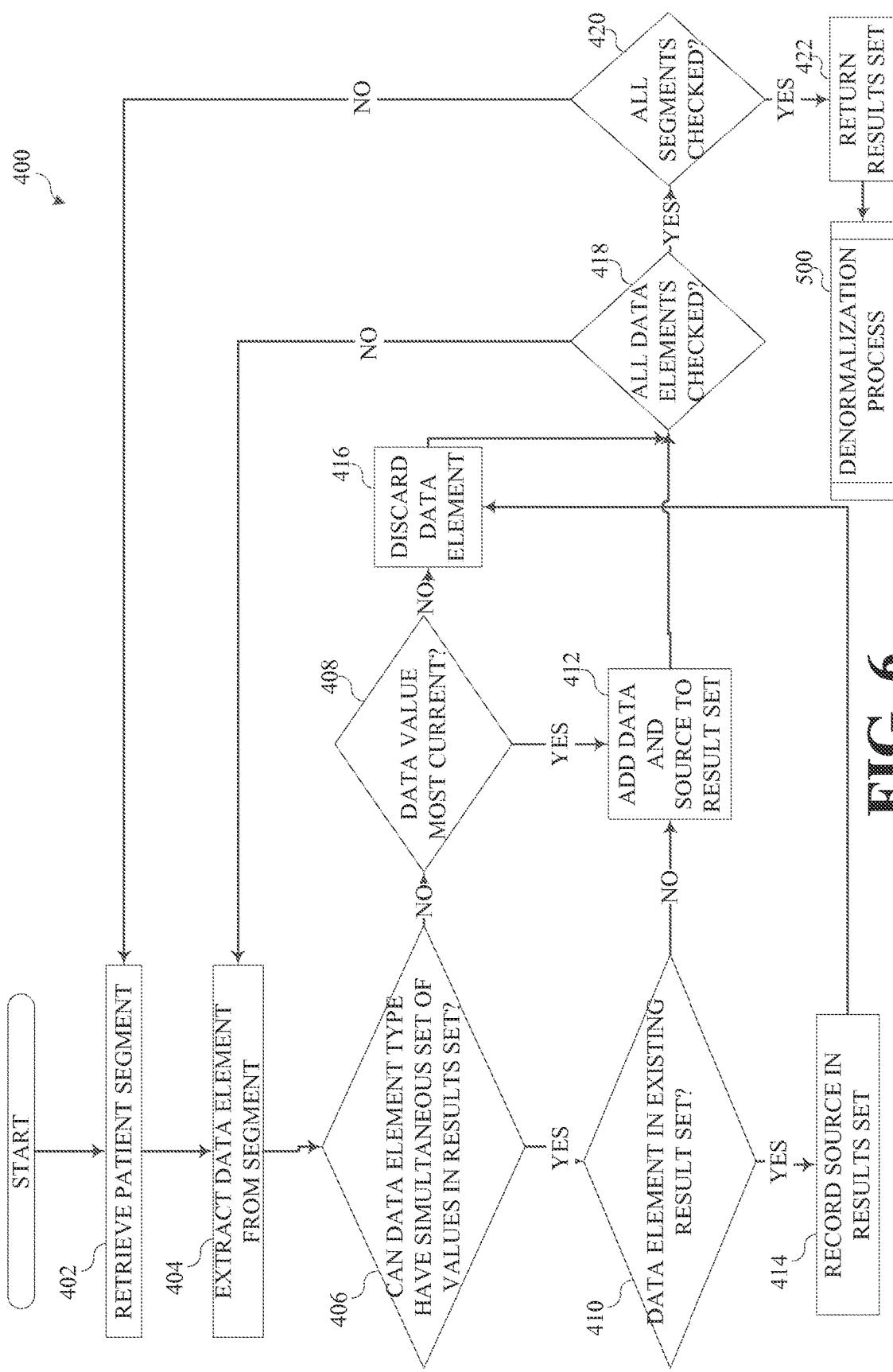
FIG. 6 is a flow chart further illustrating detailed steps of an exemplary aggregation process of FIG. 3 executed by one or more of the modules of the exemplary system architecture, according to one embodiment of the present disclosure.

Returning to the particular example above, the permissible set, after the data normalization process 300, includes two prescriptions, each for "400 mg ibuprofen." Continuing with this example, the system is configured to check to see which prescription for "400 mg ibuprofen" is the most current, then either discard the duplicate or record the source of each of the prescriptions. In this particular example, the system is configured to record the source of each of the prescriptions. Thus, in this example, the system conceptually aggregates the two normalized prescriptions to 400 mg ibuprofen from Provider 1, Provider 2 and stores this data in a database (e.g., the clinical registry database 94). FIG. 6 further depicts an exemplary embodiment of the aggregation process, which is discussed in detail below.

Figure 7:
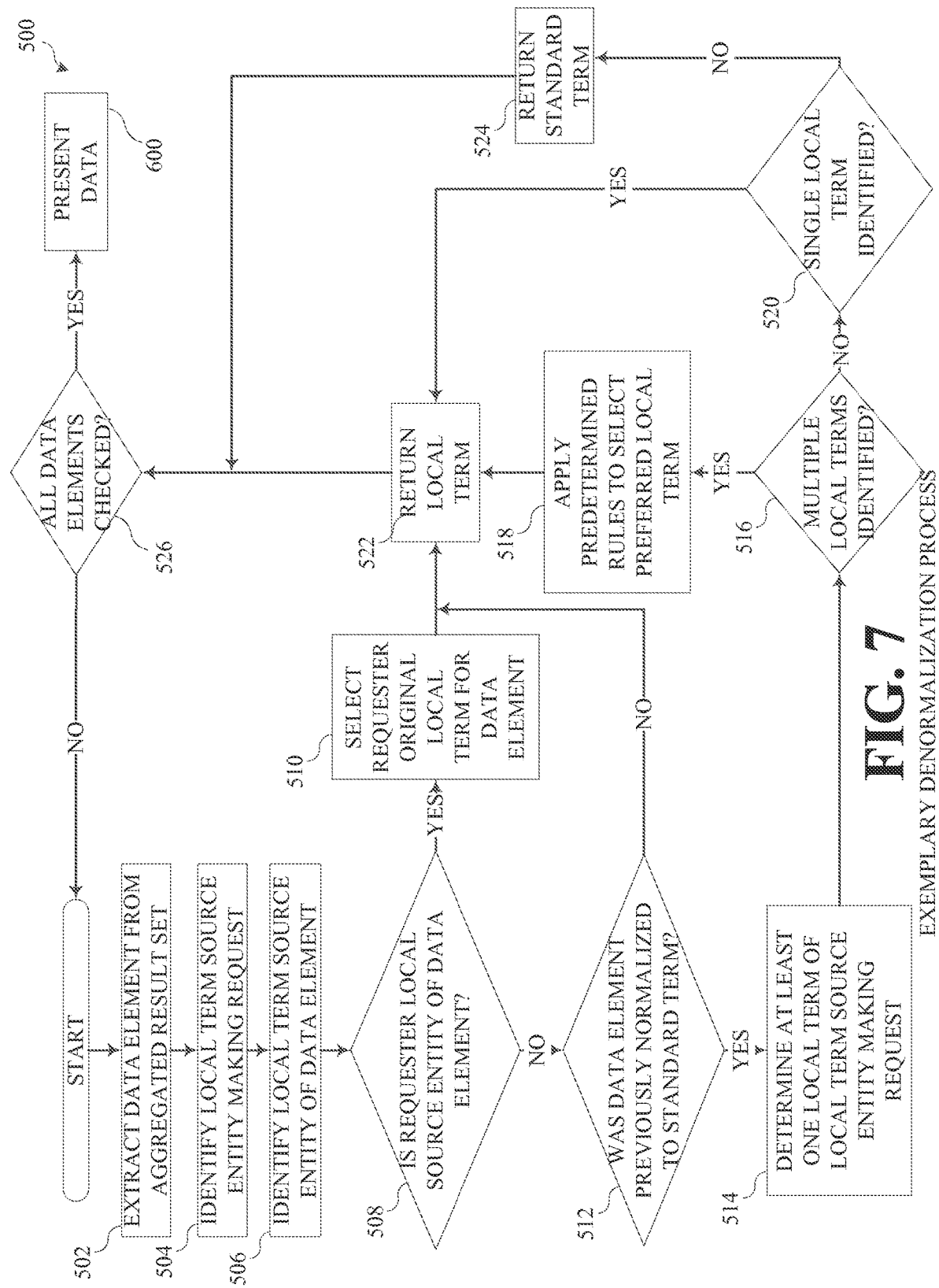
FIG. 7 is a flow chart further illustrating detailed steps of an exemplary denormalization process of FIG. 3 executed by one or more of the modules of the exemplary system architecture, according to one embodiment of the present disclosure.

At process 500, the system denormalizes the data in the permissible set. In general, according to particular embodiments, the system is configured to "denormalize" the data in the permissible set to a set of terms local to and/or preferred by the requester (e.g., the system is configured to convert the one or more terms of the permissible set to a set of terms local to the requester). Continuing with the particular example above, the system denormalizes the 400 mg ibuprofen from Provider 1, Provider 2 to a local set of terms local to the requester. In this particular example, the requester refers to prescriptions in a "name, dose" format. Thus, in this example, the system converts the stored 400 mg ibuprofen from Provider 1, Provider 2 to "ibuprofen, 400 mg" to be presented to the requester. FIG. 7 further depicts the process of denormalizing the data in the permissible set, in an exemplary embodiment, as discussed below.

Still referring to FIG. 3, at step 600, the system presents the permissible set (e.g., the normalized, aggregated, and then denormalized permissible set of data) to the requester. In various embodiments, the system is configured to present the permissible set by transmitting the data to one or more displays. In a particular embodiment, the system is configured to transmit the data to one or more displays associated with a computer system of the party that requested the data (e.g., the requester at step 102). In one or more embodiments, the system is configured to present data by transmitting the data to one or more displays associated with a party other than the requester, such as, for example, when a patient requests medical data to be sent to a specific doctor or provider.

The system may be configured to present the data by any suitable pathway. In a particular embodiment, the system is configured to transmit the data for display via the outbound traffic module 50. In further embodiments, the system is configured to transmit the data via the internal routing engine 42 (e.g., the UMIS is connected to a display and the data is directly displayed by the UMIS), and/or any other suitable mechanism. Further, it should be mentioned that in one or more embodiments, the UMIS may identify the permissible segments, normalize, aggregate, denormalize, and display the data in virtually real-time.

Identifying Permissible Segments

FIG. 4 further expands upon process 200, above, and depicts an exemplary permissible segment identification process 200 for identifying segments of the retrieved data which are to be displayed to a requester (e.g., the requester in 102, above). Starting with step 202, the system retrieves a segment (e.g., the first segment, the next segment to be checked, etc.) of data from a provider or other information source. The retrieved segment, as discussed above, may be a determined portion of data viewable by the requester (e.g., determined by what data the requester is permitted to view).

In various embodiments, the system is configured to retrieve the segment via a local UMIS module (e.g., the local UMIS module 18) that is operatively coupled to a computer system of the provider. In further embodiments, the system is configured to retrieve the segment from the provider, without the use of the local UMIS (e.g., wherein the provider does not have a local UMIS operatively coupled to their computer system).

The system, according to particular embodiments, is configured to retrieve the segment at least partially in response to receiving the request from the requester to present the data (e.g., at step 102). In some embodiments, the system is configured to substantially automatically (e.g., automatically) retrieve the segment of data from the provider according to a predetermined schedule (e.g., the system is configured to display data associated with a patient or a number of patients to a particular requester on a schedule, such as every month, every six months, etc.) and/or substantially automatically (e.g., automatically) based on one or more trigger events (e.g., a trigger transmitted to the system based on an action, such as a change in patient information). It should be understood, in light of this disclosure, that the system may be configured to retrieve the segment in response to any suitable factor.

The system may be configured to retrieve any suitable segment of data. According to particular embodiments, the segment includes a specific category of information about a patient, such as a prescription, one or more related prescriptions, all the prescriptions associated with the patient, various diagnoses (which may be segmented into diagnoses by category, by provider, etc.), etc.

In various embodiments, the segment includes one or more data elements, such as one or more data elements associated with one or more prescriptions associated with the particular patient. In one or more embodiments, the segment includes a number of various prescriptions associated with a particular diagnosis of the particular patient (e.g., any or all of the drugs prescribed to the particular patient for a specific aliment or disease). In further embodiments, the segment includes demographic data associated with the particular patient, such as age, sex, address, etc. In still further embodiments, the segment includes other information associated with the particular patient, such as allergy information, emergency contact information, etc.

The system may be configured to retrieve the segment from any suitable provider. According to a particular embodiment, the system is configured to retrieve the segment from a medical provider, such as, for example, a clinic, a doctor (e.g., a family practitioner, etc.), a hospital, an urgent care provider, a psychiatrist, etc. In one or more embodiments, the system is configured to retrieve the segment from a secondary medical provider, such as a pharmacist, a physical therapist, etc. In further embodiments, the system may be configured to retrieve the segment from one or more computer system associated with the UMIS, such as the UMIS demographics data module 80, etc. In still further embodiments, the system is configured to retrieve the segment from one or more other suitable sources, such as, for example, one or more vendors, one or more EHR/EMR databases, one or more provider systems (e.g., the third-party system 36), one or more insurer systems, one or more payer systems, etc.

At step 204, the system determines whether the retrieved patient segment is sharable to the requester (e.g., the data included may be restricted as to with whom the data can be shared). In various embodiments, the retrieved patient segment is restricted by the Health Insurance Portability and Accountability Act ("HIPAA") and/or other privacy regulations. In some embodiments, the retrieved patient segment is restricted by the patient (e.g., the patient can submit to the UMIS with whom they wish any or all of his or her data to be shared). In particular embodiments, the retrieved patient segment is restricted by a predetermined set of rules associated with the UMIS (e.g., a set of privacy rules custom to the UMIS). In further embodiments, the retrieved patient segment is restricted by the source provider (e.g., the provider may include instructions and/or rules regarding with whom the provider allows the data (or a portion of the data) to be shared).

The system may be configured to determine whether the retrieved patient segment is sharable to the requester in any suitable way. In various embodiments, the system is configured to compare the type of requester (e.g., the requester is a private provider, a hospital, a pharmacy, a family member of the particular patient, etc.) with any restrictions on sharing the segment (e.g., where the restrictions are by type of requester, such as the segment is sharable to providers, but not to patients or patient relatives). In particular embodiments, the system is configured to compare the content of the request with restrictions associated with the retrieved patient segment (e.g., the request to for one or more prescriptions compared to a restriction that prescriptions are not to be shared). It should be understood, in light of this disclosure, that the system may be configured to make the determination of whether the retrieved patient segment is shareable by any suitable mechanism, including, but not limited to one or more look-up tables, one or more algorithms, etc. Additionally, it should be understood that the patient segment may be restricted by more than one of, and/or any combination of, any of the restrictions discussed above.

At step 206, in response to determining that the retrieved patient segment is not sharable to this requester, the system discards the retrieved patient segment. The system determines whether all segments have been checked at step 214.

Continuing with step 208, in response to determining that the retrieved patient segment is shareable to the requester, the system determines whether the patient segment is viewable by the requester. The retrieved patient segment may be restricted to who may view the retrieved patient segment in any of the ways discussed above at step 204 (and/or any other suitable way). The system may be configured to determine whether the retrieved patient segment is viewable to this requester in any of the ways the system is configured to determine whether the retrieved patient segment is sharable to the requester (e.g., at step 204) and/or in any other suitable way.

At step 210, in response to determining that the retrieved patient segment is not viewable by the requester, the system discards the retrieved patient segment and determines whether all segments have been checked at step 214.

At step 212, in response to determining that the retrieved patient segment is viewable by the requester, the system includes the retrieved segment in a permissible set. In a particular embodiment, the permissible set is a set of segments to be presented to the requester (e.g., after being normalized, aggregated, and denormalized, as described below).

The system may be configured to compile the permissible set in any suitable way. In various embodiments, the system is configured to compile the permissible set as a list of one or more segments. In further embodiments, the permissible set is compiled as a table of the one or more permissible segments. In still further embodiments, the permissible set is compiled as a one or more separate files each including a permissible segment.

At step 214, the system determines whether all segments have been checked. In response to determining that all segments have not been checked, the system is configured to return to step 202 (e.g., and retrieve the next segment to be checked). In response to determining that all permissible segments have been checked, the system normalizes the permissible segments at process 300, as further discussed below. It should be understood in light of this disclosure that, in various embodiments, it is possible that no permissible segments may be found for a particular requester (e.g., where a person does not have permission to view any of a patient's medical records).

Normalizing Data

Figure 5:
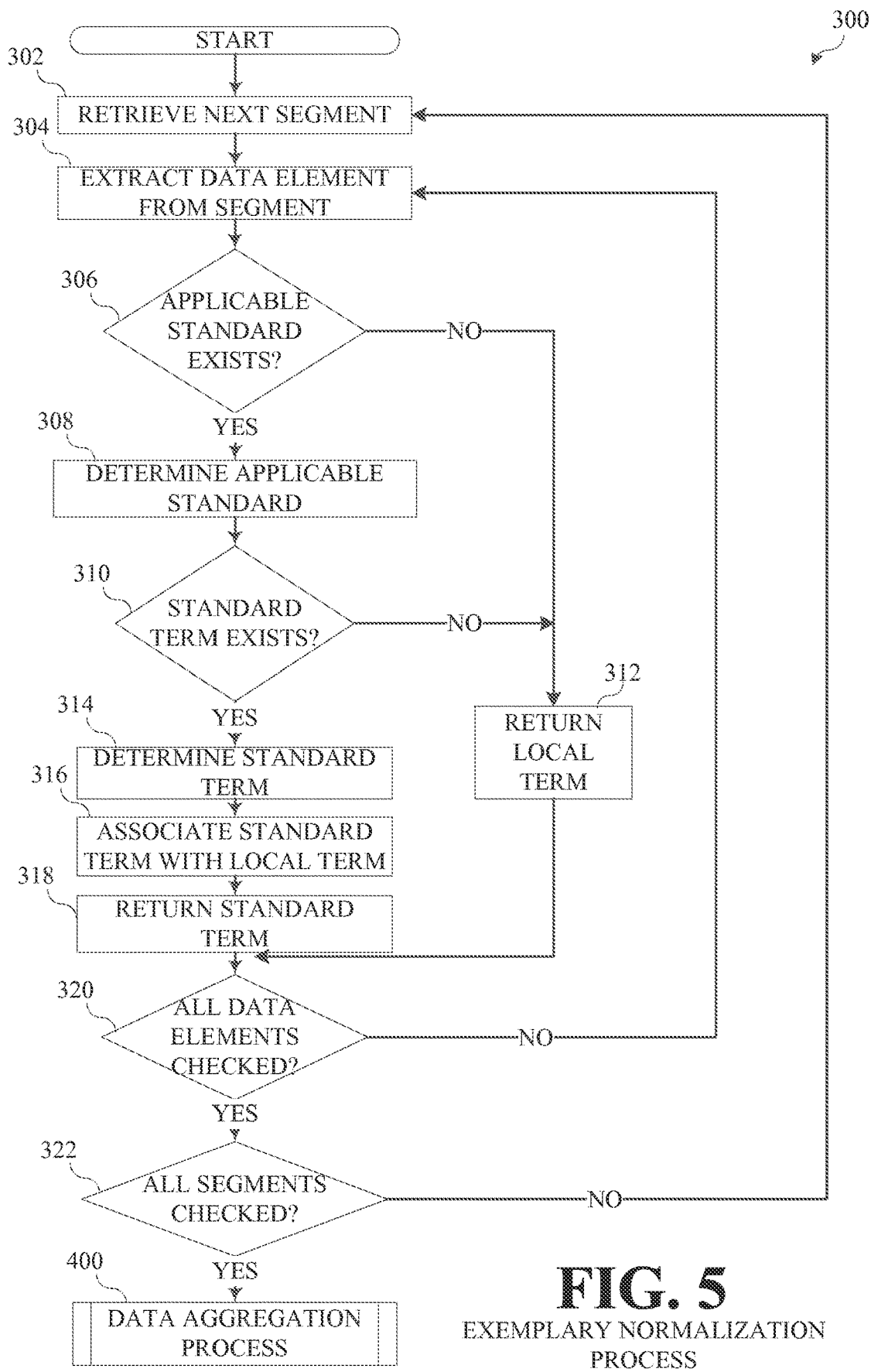
FIG. 5 is a flow chart further illustrating detailed steps of an exemplary normalization process of FIG. 3 executed by one or more of the modules of the exemplary system architecture, according to one embodiment of the present disclosure.

Turning to FIG. 5, in one embodiment, the system normalizes the data included in the permissible set (e.g., the set of segments sharable to and viewable by the requester) via a data normalization process 300. The system begins, at step 302 by retrieving the next segment of the permissible set (e.g., the first segment of the permissible set of segments to be normalized, the second segment of the permissible set of segments to be normalized, etc.). The system may be configured to retrieve the next segment of the permissible set in any suitable way, including, but not limited to any of the ways discussed above at step 202 (FIG. 2) or in any other suitable way. In a particular example, the system is configured to retrieve the first segment of a series of data segments arranged in a table (e.g., the permissible set is arranged in a table).

It should be understood, in light of this disclosure, that the retrieved next segment may be any suitable segment of data. In a particular embodiment, the retrieved next segment is the entire retrieved segment from the provider (e.g., discussed at step 202, above). In some embodiments, the retrieved next segment is a portion of the retrieved segment from the provider (e.g., the retrieved next segment is a single prescription where the retrieved segment from the provider includes a series of prescriptions from the provider).

At step 304, the system extracts one or more data elements from the retrieved segment. In various embodiments, the system is configured to extract the one or more data elements by parsing the retrieved segment (e.g., the system separates each part of the retrieved segment by one or more delimiters, such as a space, a comma, a semicolon, etc.). It should be understood, in light of this disclosure, that the system may be configured to extract the one or more data elements in any suitable way.

The one or more data elements may be any suitable data elements. In a particular embodiment, the one or more data elements include a local term, which may be, for example, a term used by a provider to describe something about the particular patient (e.g., a prescription, a diagnosis, such as "Heart Attack", demographic information, etc.). In various embodiments, each of the one or more data elements is a single word or number (e.g., "400" or "ibuprofen"). In further embodiments, each of the one or more data elements is a combination of words and/or numbers (e.g., "400 mg," "400 mg," "400 mg ibuprofen," etc.).

It should be noted that the system may be configured to extract any number of the one of the one or more data elements substantially simultaneously. In a particular embodiment, the system is configured to extract one of the one or more data elements (e.g., "400"). In further embodiments, the system is configured to extract a plurality of the one or more data elements (e.g., extract both "400" and "mg").

At step 306, the system determines whether an applicable standard exists for the extracted one or more data elements. In particular embodiments, the system is configured to determine whether the applicable standard exists for the extracted one or more data elements by comparing the type of data included in the one or more data elements to a listing of standards that are arranged by the type of data included in the standard (e.g., the one or more data elements are one or more immunizations and the list of standards includes an "immunization" standard). In one or more embodiments, the system is configured to determine if an applicable standard exists for the extracted one or more data elements by comparing the one or more data elements to the entries of one or more sets of standards (e.g., the system is configured to compare the data element, such as "ibuprofen," to the listings within the standards to find a standard for "ibuprofen"). In further embodiments, the system is configured to determine whether the applicable standard exists for the extracted one or more data elements by comparing the provider associated with the one or more data elements (e.g., the provider originally associated with the retrieved segments) to one or more lists of standards, where the list is organized by the type of provider. As a particular example, the system determines if an applicable standard exists for the one or more data elements by determining whether: 1) the one or more data elements were extracted from a pharmacist; and 2) an applicable standard exists for one or more pharmacist-related data elements. It should be understood in light of this disclosure that the system may be configured to determine whether an applicable standard exists for the extracted one or more data elements by any other suitable way as will be recognized by one of skill in the art.

It should be understood that the system may use any suitable applicable standard, including, but not limited to proprietary standards. In various embodiments, the system may use SNOMED CT, CVX, MVX, LOINC, RxNorm, CPT, etc. It should also be understood that each of the one or more data elements may be subject to different applicable standard. For example, a diagnosis-related data element may be subject to the SNOMED CT standard and an immunization data element may be subject to the CVX standard.

According to various embodiments, the system may be configured to store one or more listings of one or more applicable standards within the UMIS. In particular embodiments, the system is configured to retrieve the applicable standards from an external database.

At step 308, in response to determining that an applicable standard exists for the extracted one or more data elements, the system determines the applicable standard for the one or more data elements (e.g., if there is more than one applicable standard relevant to the one or more data elements). The system may be configured to determine the applicable standard for the one or more data elements in any suitable way, such as, for example, by determining which applicable standard is the most common applicable standard for the one or more date elements (e.g., if there is more than one existing applicable standard for a particular local term included in the one or more data elements, the system is configured to determine the most common), by accessing a preferred and/or preconfigured list of standards, and/or by complying with a government mandated standard. It should be understood, in light of this disclosure, that the system may be configured to have access to a single set of standards for one or more certain types of local terms included in the one or more data elements (e.g., one set of applicable standards for diagnosis local terms, such as SNOMED CT).

At step 310, the system determines whether a standard term, of the determined applicable standards, exists for the one or more extracted data elements (e.g., within the determined applicable standards from step 308). In various embodiments, the system is configured to search within the determined applicable standards for the one or more extracted data elements (e.g., the system searches the determined applicable standards for "Heart Attack" to locate the standard term equivalent). In one or more embodiments, the system is configured to search a look-up table associated with the determined applicable standards to locate the one or more extracted data elements (or a determined equivalent).

At step 312, in response to determining either 1) that no applicable standard exists for the one or more extracted data elements or 2) that no standard term exists for the one or more extracted data elements, the system returns the one or more local terms included in the one or more extracted data elements (e.g., the system does not use a standard term), and, in some embodiments, instead uses a local term. The process continues to step 320, as discussed below.

At step 314, in response to determining that a standard term exists for the one or more extracted data elements, the system determines the standard term. In various embodiments, the system is configured to determine the standard term by comparing the one or more data elements with one or more listings of elements associated with the applicable standard. In a particular example, the applicable standard is a standard for diagnosis and the one or more data elements includes an entry for "Heart Attack." Continuing with this example, the system is configured to locate "Heart Attack" within the applicable standard listing and find the corresponding applicable standard for "Heart Attack." Still continuing with this example, the system locates the applicable diagnosis standard of "Myocardial Infarction." In other embodiments, the standard term of step 314 is determined at step 310.

At step 316, the system associates the standard term with the one or more data elements (e.g., the one or more local terms). In various embodiments, the system is configured to associate the standard term with the local term by replacing the one or more data elements with the standard term. In particular embodiments, the system is configured to associate the standard term with the local term by linking the standard term to the local term in memory. In further embodiments, the system is configured to associate the standard term with the local term by adding an indication of the standard term to the one or more segments from which the one or more data elements have been extracted.

At step 318, the system returns the standard term for each of the one or more extracted data elements. In particular embodiments, the system is configured to replace the one or more extracted data elements with the associated standard term in the permissible data set. In this way, in some embodiments, the system normalizes the permissible data set from a set of local terms (e.g., the extracted data elements) to a set of standard terms.

At step 320, the system determines whether all data elements of the retrieved segment have been checked. In response to determining that all data elements have not been checked, the system returns to step 304 (e.g., to extract the next one or more data elements from the retrieved segment).

At step 322, in response to determining that all data elements of the retrieved segment have been checked, the system determines whether all segments of the permissible set of segments have been checked. In response to determining that all segments of the permissible set of segments have not been checked, the system returns to step 302 (e.g., to retrieve the next unchecked permissible segment).

At step 326, in response to determining that all retrieved segments of the permissible set of segments have been checked, the system aggregates the data via process 400, as further detailed in FIG. 6.

Aggregating Data

Turning to FIG. 6, an exemplary data aggregation process is shown in which the system aggregates the normalized data of the permissible set. In general, in various embodiments, the system is configured to check each data element of the normalized data set to determine the most current data and return a normalized, aggregated results set. Beginning at step 402, the system retrieves a segment of the permissible set (e.g., a segment of the normalized permissible set from above). The system may be configured to retrieve the normalized segment of the permissible set in any suitable way, including, but not limited to, the ways the system is configured to retrieve a segment above in steps 202 and 302.

At step 404, the system extracts one or more aggregation data element values from the segment, wherein the one or more aggregation data element values are of a particular type. It should be understood, in light of this disclosure, that the system may be configured to extract the one or more aggregation data element values from the segment in any of the ways (or other ways) the system is configured to extract the one or more data elements at step 304.

The particular type of data may be any suitable category into which data is categorized. In various embodiments, the particular type of data includes one or more current or previous medications prescribed to the patient (e.g., the respective data value(s) for this type of data may be, for example, Tylenol®, 400 mg Tylenol®, ibuprofen, 200 mg ibuprofen, oxycodone, Viagra®, Lipitor®, NyQuil®, Celebrex®, etc.). In one or more embodiments, the particular type of data includes a preferred name of the patient (e.g., the respective data value may be John, Bob, etc.). In further embodiments, the particular type of data includes a social security number of the patient. In still further embodiments, the particular type of data includes, for example, a birthday of the patient and/or other demographic information associated with the patient, one or more relatives of the patient, one or more diagnoses of the patient (e.g., the corresponding data value(s) may be flu, heart disease, etc.), etc.

It should be understood that the system extracts data elements to compile a results set of stored values (e.g., a normalized, aggregated results set). Here, at step 404, the results set may or may not already consist of data to be presented and/or that needs to be verified. The system may be configured to store values for the results set in any suitable way. In various embodiments, the system is configured to store values for the results set by associating the values with the results set in a look-up table. In a particular embodiment, the system is configured to store values for the results set by assigning one or more indicators and/or locations to the values that associate the values with the results set.

At step 406, the system determines whether the results set (e.g., to be returned to the requester) is permitted to store simultaneous values for the type of value of the one or more aggregation data elements. In various embodiments, system is configured to determine whether the results set is permitted to store a predetermined number of values for a given type of data element. By way of a particular example, the extracted one or more aggregation data element values (e.g., extracted at step 404) is of the social security data type and the corresponding value is a particular social security number (e.g., XXX-XX-XXXX) associated with the particular patient. Continuing with this particular example, the system is configured to determine whether the results set is permitted to store more than one value for the patient's social security number (e.g., the social security number is the data type). Here, in this example, the system is configured to return a results set with only one social security number for the patient. Thus, in this example, the system determines that the results set is not permitted to store simultaneous values for this particular data type/data value.

The system may be configured to determine whether the results set is permitted to store simultaneous values for a particular data element in any suitable way. In various embodiments, the system is configured to recognize (e.g., by any suitable mechanism) whether the extracted one or more aggregation data elements fall into a predetermined data type (e.g., the system is configured to determine the data type of extracted data and, thus, whether the results set accepts simultaneous values for the particular results set). In one or more embodiments, the system is configured to determine whether the results set is permitted to store simultaneous values for a particular data element based on one or more preferences of the requester, which may be received and/or determined by the system (e.g., the system may receive the one or more preferences of the requester in any suitable way).

At step 408, in response to determining that the results set is not permitted to store simultaneous values for the one or more aggregation data elements, the system is configured to determine whether the one or more aggregation data element values are the most current values. In various embodiments, the system is configured to determine whether the one or more aggregation data element values are the most current values by comparing a date associated with the one or more aggregation data element values with a date associated with any data element values included in the results set. As a particular example, the extracted one or more aggregation data elements includes date metadata, which the system may compare to one or more data elements in the results set (e.g., existing data elements in the results set) to determine which data element is the most current. The system may be configured to determine whether the one or more aggregation data element values are the most current in any other suitable way, including, but not limited to: 1) comparing an element date associated with the one or more aggregation data elements with a current date (e.g., today's date as stored within the system) to determine whether the element date is within a predetermined range from the current date; and/or 2) comparing an indicator other than a date associated with the one or more aggregation data elements with a similar indicator associated with one or more data elements in the results set, etc.

At step 410, in response to determining that the results set is permitted to store simultaneous values for the type of value of the one or more aggregation data elements, the system is configured to determine whether the results set includes the one or more aggregation data elements (e.g., whether the results set substantially includes the one or more data elements or an equivalent). In various embodiments, the system is configured to determine whether the results set includes the one or more aggregation data elements by comparing the value of the one or more aggregation data elements with the value of one or more data elements in the results set (e.g., to determine if there is a match). In one or more embodiments, the system is configured to determine whether the results set includes the one or more aggregation data elements by comparing various aspects of the one or more aggregation data elements (e.g., metadata, etc.) with similar various aspects of one or more data elements of the results set (e.g., to determine if at least some portion of the various aspects of each of the aforementioned data elements (e.g., metadatas) match or are substantially similar).

At step 412, in response to determining that the one or more aggregation data element values are the most current values (e.g., at step 408) or in response to determining that the results set does not include the one or more aggregation data element values (e.g., at step 410), the system is configured to add the one or more aggregation data element values and the source of the one or more aggregation data elements to the results set. The system may be configured to add the one or more aggregation data element values to the results set in any suitable way, such as (but not limited to), by associating the one or more aggregation data element values with the results set in a look-up table, by adding an indicator to the one or more aggregation data element values such that the indicator associates the values with the results set, by adding the one or more aggregation data element values to a list associated with the results set, etc.

At step 414, in response to determining that the results set includes the one or more aggregation data elements, the system is configured to associate the source of the one or more aggregation data elements in the results set (e.g., but not, in particular embodiments, the one or more aggregation data element values). According to particular embodiments, the source is an indication of where the one or more data elements originated, such as, for example, a system associated with a hospital (if the one or more aggregation data elements are part of medical records from the hospital), a system associated with a clinic, a system associated with a private physicians office, etc.

The system may be configured to associate the source of the one or more aggregation data elements in the results set in any suitable way, including, but not limited to, the ways the system is configured to associate the one or more aggregation element values with the results set at step 412.

At step 416, in response to determining that the one or more aggregation data element values are not the most current values (e.g., step 408) or once one or more aggregation data element values are recorded in the results set (e.g., at step 414), the system is configured to discard the one or more aggregation data element values (e.g., the one or more redundant data elements).

At step 418, the system determines whether all aggregation data elements of the retrieved segment have been checked. In response to determining that all aggregation data elements have not been checked, the system returns to step 404 (e.g., to extract the next one or more aggregation data elements from the retrieved segment).

At step 420, in response to determining that all aggregation data elements of the retrieved segment have been checked, the system determines whether all segments of the permissible set of segments have been checked. In response to determining that all segments of the permissible set of segments have not been checked, the system returns to step 402 (e.g., to retrieve the next unchecked permissible segment).

In response to determining that all segments of the permissible set of segments have been checked, the system, at step 422 returns the results set and denormalizes the results set (e.g., the normalized, aggregated results set) via the denormalization process 500, as further detailed in FIG. 7.

Denormalizing Data

Turning to FIG. 7, the system, in general, denormalizes the aggregated results set (as discussed above in FIG. 6) via a data denormalization process 500. In this way, the system can present an aggregated results set that is (at least partially) in the requester's local and/or expected or preferred terms (e.g., "denormalized" terms). It should be noted, that in various embodiments, the aggregated results set includes only aggregated data that is viewable to the requester. Thus, the system, in this (and other) embodiments, is configured to extract data elements, but not segments.

Beginning at step 502, the system is configured to extract one or more extraction data elements from the aggregated results set (e.g., from FIG. 6). The system may be configured to extract the one or more extraction data elements from the aggregated results set in any suitable way, including, but not limited to any of the ways described above in steps 202, 302, and 402.

At step 504, the system identifies the requester (e.g., which requester made the request at step 102). In various embodiments, the system is configured to identify the requester based on information included with the request at step 102 (e.g., the requester is identified when the request is made and/or an indication of the requester is included with the permission set). In one or more embodiments, the system is configured to identify the requester in any other suitable way, such as, by third-party data (e.g., the system is configured to check the identity of the requester via a commercial service or some other means), by sending the requester an identification request and receiving a response, etc.

At step 506, the system is configured to identify the supplier entity that supplied the extracted data element (e.g., the data element extracted at step 502). In various embodiments, the system is configured to identify the supplier entity by an indication of the supplier entity included with the data element (e.g., the data element has embedded data that includes the supplier entity). According to particular embodiments, the system is configured to identify the supplier entity by the data included within the data element (e.g., the data element includes an indication that ibuprofen, 400 mg was provided by Provider 1, where "Provider 1" is the supplier entity as discussed above). In further embodiments, the system may be configured to identify the supplier entity by the type of information within the extracted data element (e.g., the data element includes a type of information specific to a particular supplier entity, such as certain prescriptions are only supplied by certain types of clinics). It should be understood, in light of this disclosure, that the system may be configured to identify the supplier entity in any suitable way, including, but not limited to, any combination of the ways discussed above.

A step 508, the system is configured to determine whether the requester is the supplier entity. In various embodiments, the system is configured to determine whether the requester is the supplier entity by comparing the name of the requester and name of the supplier entity (e.g., by comparing "Dr. Jones" and "Providence Hospital"). According to particular embodiments, the system is configured to determine whether the requester is the supplier entity by converting the requester and the supplier entity to one or more codes then comparing the coded requester to the coded supplier entity (e.g., the system converts "Dr. Jones" to 001 and "Providence Hospital" to 032 and then compares 001 to 032). In further embodiments, the system is configured to determine whether the requester is the supplier entity by converting the requester and the supplier entity to terms that indicate which one or more local term sets the requester and the supplier entity each utilize, then comparing the local term set of the requester with the local terms set of the supplier entity (e.g., the system is configured to convert "Dr. Jones" to the local terms set "Set A" and "Providence Hospital to "Set A" (in the case where they use the same local terms for prescriptions, demographics, etc.) and then compares "Set A" to "Set A").

In response to determining that the requester is the supplier entity, at step 510, the system is configured to select the original local term for the data element (e.g., the one or more terms the data set included when the data was retrieved as part of the retrieved segment at step 202). The system may be configured to select the original local term for the data element in any suitable way, including, but not limited to, by retrieving the data element from the originally retrieved data segment, by retrieving the data segment again (e.g., in the same way, or other ways, as those described in step 202), by retrieving the data element from memory (e.g., as stored in one or more databases associated with the UMIS), etc.

In response to determining that the requester is not the supplier entity, at step 512, the system is configured to determine whether the data element was previously normalized to a standard term (e.g., at step 316). In various embodiments, the system is configured to determine whether the data element was normalized to the standard term by checking for an indicator that the data element was normalized to the standard term (e.g., if the system is configured to add an indicator, such as metadata, indicating that the data element has been normalized at step 316). In one or more embodiments, the system is configured to determine whether the data element was normalized to the standard term by checking a log associated with the system, where the logs keeps track of all normalized terms in an existing permissible set. In further embodiments, the system is configured to determine whether the data element was normalized to the standard term by comparing the data element to one or more standard terms (e.g., if the data element matches the one or more standard terms, then it has been normalized).

In response to determining that the data element was normalized to the standard term, at step 514, the system is configured to determine at least one local term of the requester for the data element (e.g., which term the requester uses for "heart attack" or "ibuprofen"). The system may be configured to determine the at least one local term of the requester for the data element in any suitable way, such as, for example, by extracting the appropriate at least one local term from a local data set that was sent by (or retrieved from) the requester (e.g., with the request at step 102) and comparing the at least one local data term to the extracted at least one local term and/or by comparing the data element to one or more databases of local terms (e.g., one or more of the databases depicted in FIGS. 1 and 2).

It should be noted that, according to particular embodiments, the system may be configured to determine only one local term for the data element. In further embodiments, the system determines more than one local term for the data element. As a particular example, the requestor may use more than one term to reference the same patient aliment, such as "Heart Attack" and "Myocardial Infarction" for heart attacks.

The system continues, at step 516, by determining whether multiple local data terms were identified, as discussed immediately above. In response to determining that multiple data terms were identified, the system is configured to, at step 518, apply a predetermined set of rules to select a preferred local term for the data element. The system may be configured to apply any suitable predetermined set of rules to select the preferred local term for the data element, such as, for example, selecting as the preferred local term the most commonly used term for the data element (e.g., the requester uses both "Heart Attack" and "Myocardial Infarction," but more frequently uses "Heart Attack"), selecting the preferred local term from a list received from the requester, selecting the preferred local term from a list received from an entity other than the requester (e.g., a third-party affiliated with the requester, etc.), etc.

At step 522, in response to determining: 1) the data was not previous normalized to a standard term (e.g., at step 512); 2) multiple local terms were not identified (e.g., at step 516); and 3) that the single local term was identified (e.g., at step 520), the system returns the local term (as determined in step 510 and 518) to be included in the results set.

Continuing with step 524, in response to determining that no single local term was identified, the system returns the standard term for the data element (e.g., the system is configured to not to change the term from the standard term to a local term). As a particular example, assume the aggregated (and normalized) results set contains the data element value "Heart Attack." Continuing with this example, the system determines that there is no local term for "Heart Attack," thus, the system returns the standard term "Heart Attack" for the results set.

At step 526, the system determines whether all data elements have been checked. If all data elements have been checked, then the system presents the data as described at step 600, above. If the data elements have not all been checked, then the system returns to step 502 and extracts the next data element from the aggregated results set.

Outdated Demographics and Clinical Segments

Figure 8:
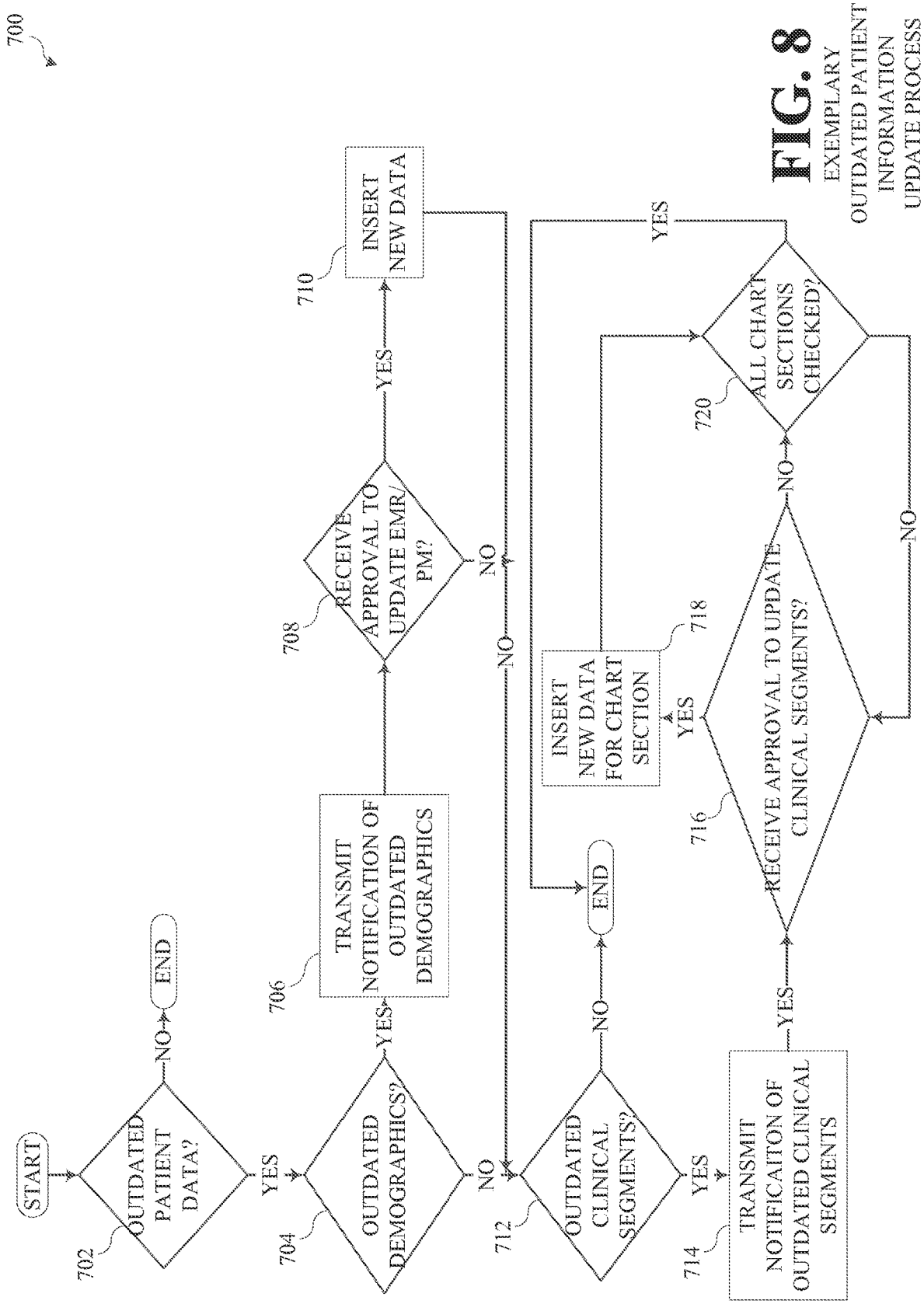
FIG. 8 is a flow chart illustrating detailed steps of an exemplary outdated patient information update process by the UMIS according to a particular embodiment.

FIG. 8 depicts an exemplary process for updating demographics and/or clinical segments, which may be outdated (e.g., incorrect, missing information, etc.). According to a particular embodiment, FIG. 8 generally relates to updating patient data at a provider system (e.g., receiving information at a local UMIS from the UMIS) and updating the records of the local electronic medical records/practice management ("EMR/PM") system.

Starting with step 702, the system determines whether particular patient data is outdated. In various embodiments, the particular patient data is demographic data. In particular embodiments the particular patient data is clinical data (e.g., prescription data/information, previous diagnoses, etc.). In further embodiments, the particular patient data is other information related to the particular patient such as contact information of relatives of the particular patient, medical history of the particular patient, etc.

The system may be configured to determine that the particular patient data is outdated in any suitable way. According to particular embodiments, the system is configured to determine whether the particular patient data is outdated by comparing a date associated with received patient data with a date associated with the particular patient data (e.g., the system is configured, in at least one embodiment, to receive patient data and check to see whether the received patient data is more current the existing patient data). In one or more embodiments, the system is configured to determine that the particular patient data is outdated by receiving a suitable indication (e.g., any suitable indication, such as a trigger mechanism, etc.) that the particular patient data has been updated (e.g., changed) at a corresponding location, such as the UMIS. In further embodiments, the system is configured to determine that the particular patient data is outdated by comparing the date and/or time the particular patient data was stored with the current date and/or time to determine whether the date and/or time of the particular patient data is outside of a predetermined range of the current date and/or time (e.g., the particular patient data was updated more than two years ago as measured by the current date).

In response to determining that the particular patient data is outdated, at step 704, the system determines whether the demographics associated with the particular patient are outdated (e.g., opposed to clinical data associated with the particular patient). The demographics may be any suitable data associated with the particular patient, including, but not limited to, the particular patient's birthday, name, nickname (e.g., preferred name), address, etc.

In response to determining that the demographics associated with the particular patient are outdated, the system, at step 706, transmits a notification of the outdated demographics. In various embodiments, the system is configured to transmit the notification of the outdated demographics to a computer system associated with a third party, such as, for example, a display where a technician (a human technician) receives the notification. In one or more embodiments, the system is configured to transmit notification of the outdated demographics to any suitable computer system, such as one or more third-party providers, the particular patient (for verification), etc.

The notification may include any suitable information. In various embodiments, the notification includes an indication that the patient data is outdated. In one or more embodiments, the notification includes the indication that the patient data is outdated as well as what information is outdated (e.g., the particular patient's name, birthday, confidential personal information, etc. is outdated). In further embodiments, the notification includes the indication of outdated information along with a link to a particular page that displays the data to be updated. In still further embodiments, the notification includes the indication of outdated information along with a link that, when accessed, automatically updates the outdated particular patient demographic information with the updated patient demographic information.

It should be understood that the system may be configured to determine whether the party (e.g., the one or more third-party providers above) has permission to view/receive outdated demographics associated with the particular patient. In these (and other) embodiments, the system is configured to transmit the data upon determination the party has permission to view such data (e.g., permission based on regulations, patient preferences, etc.). As a particular example, the system may determine the particular patient's demographics are outdated (e.g., at step 704) and determine that the party to receive the notification of the outdated information is the particular patient's physician and has permission to view the demographic change.

At step 708, the system determines whether approval to update the EMR/PM system has been received (e.g., at least partially in response to transmitting the notification above). In various embodiments, the system is configured to determine whether approval to update the EMR/PM system has been received by substantially continuously checking to see if a notification of the approval has been received. In one or more embodiments, the system is configured to determine whether approval to update the EMR/PM system has been received by checking for updates in the EMR/PM system (e.g., the system is configured to determine that approval has been received via a change in the EMR/PM system). In further embodiments, the system is configured to determine whether approval to update the EMR/PM system has been received in any other suitable way.

The system may be configured to receive approval to update the EMR/PM system from any suitable entity. In various embodiments, the system is configured to receive approval to update the EMR/PM system from a third-party system. In one or more embodiments, the system is configured to receive approval to update the EMR/PM system from one or more human users (e.g., a user of the EMR/PM system takes some action that notifies the EMR/PM system to update the demographics of the particular patient).

The approval to update the EMR/PM may include any suitable information. In various embodiments, the approval includes the information (e.g., the demographic information) to be updated. According to particular embodiments, the approval to update the EMR/PM includes any suitable information such as the time and/or date the approval was received, the time and/or date the approval was sent, the system and/or user (e.g., identifying information about the approval sender such as a log-in name, IP address, etc.) that initiated the approval (e.g., sent the approval and/or otherwise notified the system), clinical data and/or other demographic data associated with the particular patient, etc.

In response to determining that the system has received approval to update the EMR/PM system, the system, at step 710, inserts the new data (e.g., the changed demographics).

In particular embodiments, the system is configured to insert the new data by replacing the previous data in specific fields (e.g., text fields or other suitable data fields). In one or more embodiments, the system is configured to add one or more new data fields and insert the new data (e.g., where the data to be inserted is new demographic data). In further embodiments, the system is configured to insert the new data by replacing all of the data in various fields associated with the particular patient (e.g., where all of the data associated with the particular patient has changed and/or there is a new patient). It should be understood by one of skill in the art that any new data fields discussed herein can be created in any suitable way by the system.

At step 712, in response to: 1) determining the demographics are not outdated (step 704); 2) determining that the system has not received approval to update the EMR/PM system (step 708); or 3) in response to inserting new data (e.g., changed demographics at step 710), the system determines whether the clinical information associated with the particular patient is outdated. The system, in various embodiments, is configured to determine whether the clinical information associated with the particular patient is outdated by comparing the data currently in the database to the information included with the received patient data. It should be understood that the system may be configured to determine whether the clinical information associated with the particular patient is outdated in any of (but not limited to) the ways the system determines whether the demographic information associated with the particular patient is outdated (e.g., at step 704). It should be understood that, in various embodiments, the clinical information may be stored according to clinical chart sections (e.g., electronic). Thus, in these (and other) embodiments, the system may be configured to determine whether the clinical information is outdated by chart section (e.g., by checking each chart section).

In response to determining that the clinical information associated with the particular patient is outdated, the system, at step 714, transmits a notification of the outdated clinical information associated with the particular patient. The system may be configured to transmit the notification of the outdated clinical information associated with the particular patient in any suitable way and to any suitable party, such as, for example, the ways the system is configured to transmit notifications described in step 706.

The system, at step 716, determines whether approval to update one or more clinical records has been received. In various embodiments, the system is configured to determine whether approval to update the one or more clinical records has been received by substantially continuously checking to see if a notification of the approval has been received. In one or more embodiments, the system is configured to determine whether approval to update the one or more clinical records has been received by checking for updates in the EMR/PM system (e.g., the system is configured to determine that approval has been received via a change in the EMR/PM system). In further embodiments, the system is configured to determine whether approval to update the one or more clinical records has been received in any other suitable way.

The system may be configured to receive approval to update the one or more clinical records from any suitable entity. In various embodiments, the system is configured to receive approval to update the one or more clinical records from a third-party system. In one or more embodiments, the system is configured to receive approval to update the one or more clinical records from one or more human users (e.g., a user of the one or more clinical records takes some action that notifies the EMR/PM system to update the one or more clinical records of the particular patient).

Approval to update the one or more clinical records may include any suitable information. In various embodiments, approval includes the information (e.g., the clinical information) to be updated. According to particular embodiments, approval to update the one or more clinical records includes any suitable information such as the time and/or date the approval was received, the time and/or date approval was sent, the system and/or user (e.g., identifying information about the approval sender such as a log-in name, IP address, etc.) that initiated the notification (e.g., sent the approval and/or otherwise notified the system), clinical data and/or other demographic data associated with the particular patient, etc.

The system may be configured to update any suitable portion of the one or more clinical records. In some embodiments, the system is configured to update a particular chart section of the EMR/PM (e.g., the system checks each chart section of the EMR/PM). In various embodiments, the system may be configured to update a specific category of clinical information, such as, for example, various consultations, medication, and/or treatment received by the patient, one or more lab reports, various care plans prescribed/planned for the particular patient, etc. In one or more embodiments, the system may be configured to update more than one chart section (e.g., the system is configured to check more than one and/or all chart sections at once).

In response to determining that approval to update one or more clinical records has been received, the system, at step 718, inserts the clinical information (or a portion of the clinical data) for the particular chart section. The system may be configured to insert the clinical information in any suitable way, such as, for example, the ways in which information is inserted in step 710.

In response to determining that approval to update one or more clinical records has not been received, the system, at step 720, determines whether all chart sections have been checked. The system may be configured to determine whether all of the chart sections have been checked in any suitable way, including, but not limited to, ways substantially similar to the ways in which the system determines whether all the data elements have been checked at step 526 (FIG. 7).

Data Flow

Figure 9:
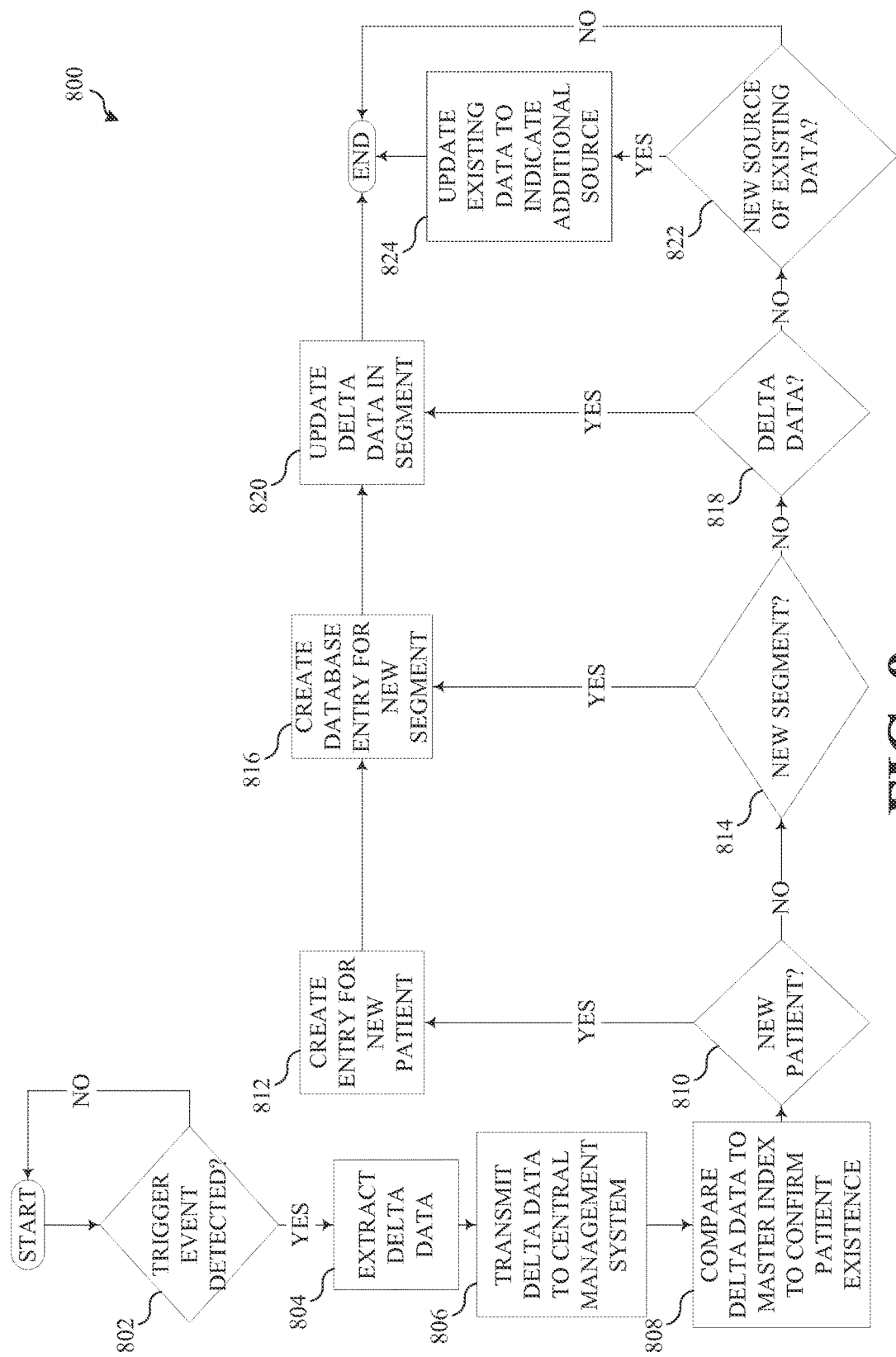
FIG. 9 is a flow chart illustrating detailed steps of an exemplary patient information update process of the UMIS according to a particular embodiment.

FIG. 9 depicts an exemplary data update process 800 for checking and updating patient data within the UMIS and exemplary environment 5. Beginning at step 802, the system detects a trigger event. In various embodiments the trigger event is in response to an update to patient information in a vendor's or provider's (e.g., EHR provider, healthcare provider, etc.) patient database. The update to the patient information may be any suitable update, including, but not limited to, an update to one or more patient's demographics, one or more patient's prescriptions, one or more patient's appointment schedules, etc.

In various embodiments, the system is configured to detect the trigger event via a local UMIS module that is part of the vendor's computing system (e.g., the local UMIS module 18). In related embodiments, the system is configured to detect the trigger event by receiving the trigger event (or an indication of the trigger event) from a vendor's or provider's database (e.g., the vendor's database is configured to send a message and/or notification that an update has occurred) at the local UMIS module. In further embodiments, the system is configured to (via the local UMIS module) regularly scan and/or search the vendor's, provider's or other third party's database for the changed data.

According to particular embodiments, the system is configured to detect the trigger event without the use of a local UMIS module. In these (and other) embodiments, the system is configured to detect the trigger event in any suitable way, such as, for example, by scanning the vendor's database for regular changes (e.g., with permission from the vendor) and noting changes, by receiving a report (e.g., a regular report) from the vendor indicating changes, by detecting the trigger event on a third-party computer system associated with the vendor, etc.

At step 804, in response to detecting the trigger event, the system extracts the changed data (e.g., "delta data") from the vendor (e.g., the local archive database 24). According to particular embodiments, the system is configured to extract the changed data by finding the changed data within the vendor database and/or finding the changed data within a portion of the vendor's computer system that is hosted by the UMIS (e.g., the local UMIS module 18). In various embodiments, the local UMIS module 18 extracts the changed data and transmits the changed data to the UMIS. In further embodiments, the system is configured to receive (opposed to extracting) the changed data from the vendor (e.g., with the trigger event).

At step 806, the system is configured to transmit the changed data to the central management system. In various embodiments, the system is configured to transmit the exchanged data to the central management system (e.g., the UMIS 40) by one or more networks (e.g., the one or more networks 34) and/or any other suitable software/hardware, such as an outbound data transport (e.g., outbound data transport 12), an outbound secure messaging transport (e.g., outbound messaging transport 15), and/or an outbound data engine that is part of the local UMIS module (e.g., outbound data engine 19).

At step 808 and 810, in response to receiving the changed data, the system determines whether the patient associated with the changed data exists in a master index (e.g., where the changed data is a change in a patient's demographic information, the system confirms the patient has an existing record in the master index). In various embodiments, the system is configured to determine whether the patient associated with the changed data exists in the master index by comparing the patient information included with the changed data to the master index to confirm whether the patient associated with the changed data exists within the master index (e.g., the master index includes a list of patient names and/or any other identifiable information associated with the patient). According to particular embodiments, the system is configured to determine whether the patient associated with the changed data exists in the master index by normalizing the changed data (e.g., as described in FIG. 5, steps 300 to 322) to the format and/or terms of the UMIS and then comparing the normalized changed data to the master index.

At step 812, in response to determining the patient associated with the changed data does not exist in the master index (e.g., the data corresponds to a new patient), the system creates a new entry for the patient. The system may be configured to create the new entry for the patient in any suitable way, such as by writing the patient's name in the master index, by assigning the patient an identifier and writing the identifier in the master index, by writing patient information to one or more databases (e.g., the demographic registry 84), etc. The system then continues to step 816 as further described below.

In response to determining that the patient associated with the changed data exists within the master index, the system, at step 814 determines whether the changed data includes a new segment of data. The new segment of data may be, for example, any suitable segment of data as further described above at step 202.

The system may be configured to determine whether the changed data includes the new segment of data in any suitable way. In various embodiments, the system is configured to determine whether the changed segment includes the new segment of data by comparing the one or more segments of data included in the changed data to one or more segments stored in the UMIS associated with the patient. In particular embodiments, the system is configured to determine whether the changed segment includes the new segment of data by comparing information associated with the segment with the one or more segments stored in the UMIS (e.g., the system compares the type of segment to the types of segments included in the UMIS, where, for example, the data associated with the patient can include only one of each segment (or only one of this specific segment).

In response to determining that the changed data includes the new segment of data, the system, at step 816, creates a new database entry for the new segment of data (e.g., and associates the new segment of data with the patient). The system may be configured to create a new database entry for the new segment in any suitable way, including, but not limited to, writing the new segment of data in memory and associating the new segment of data with the patient.

In response to determining that the changed data does not include a new segment of data (e.g., the changed data only includes one or more existing segments), the system, at step 818 determines whether the changed data exists in the existing one or more existing segments (e.g., if the change has already been recorded within the database). In response to determining that the changed data does not exist in the one or more existing segments, the system, at step 820, updates the changed data in the one or more existing segments.

In response to determining that the changed data exists in the existing one or more existing segments (e.g., at step 818) the system, at step 822 determines whether the changed data, is from a new source (e.g., a different entity has provided the changed data than the entity that provided the corresponding existing data). In various embodiments, the system is configured to determine whether the changed data is from the new source by comparing the source of the existing data (e.g., data in the one or more existing segments) with the source of the changed data. In further embodiments, the system is configured to determine whether the changed data is from the new source in any other suitable way, such as, for example, by comparing the format of the changed data with the format of existing data in the one or more existing segments (e.g., wherein the format of data can determine the source of the data), etc.

In response to determining that the changed data is from a new source (e.g., at step 822), the system, at step 824, indicates the changed data is from an additional source (e.g., in addition to the source already recorded with the corresponding data in the one or more existing segments). In response to determining that the changed data is not from a new source (e.g., it is from the same source as the corresponding data in the one or more existing segments), the system discards the changed data.

It should be understood, in light of this disclosure, that the system may receive a data change and subsequently discard the data change without changing the corresponding data in the UMIS. For example, the system receives a data change originating from a first provider, but the data related to the data change has already been updated in the UMIS. In this example, the data related to the data change could have already been updated for a number of reasons, such as because another provided updated the data first, because the patient updated the data via a patient portal, etc.

Exemplary Terminology and Standards

FIGS. 10A, 10B, and 10C depict exemplary standard terminology and how such terminology may be determined (e.g., which standard or standards may be used to normalize which local terms).

FIG. 10A depicts an exemplary hierarchical determination of terminology. As shown, the organization 1002 influences the terminology used by the practice group 1004 (terminology flows from the organization to the practice group). The organization 1002 may be any suitable organization, such as a standards setting organization, a regional, national or international organization, a hospital, a hospital system, and/or a physician practice that influences the use of terminology (American Medical Association, American Cancer Society, a regional hospital system, etc.), etc. Further, the organization 1002 may influence and/or determine the use of terminology of the practice group 1004 in any suitable way, such as through rule making, setting standards, encouraging and/or enforcing use of certain terms, etc.

As shown in FIG. 10A, the practice group 1004 may influence and/or determine use of terminology of a location 1006. For example, the practice group 1004 (which may be any suitable practice group, such as surgeons, general practitioners, pharmacists, etc.) may influence the use of one or more terms of the location 1006 (e.g., a region, a city, a state, an area, etc.) in similar ways that the organization 1002 influences the use of terminology by the practice group 1004.

The location 1006 may influence and/or determine the use of terminology by a provider 1008 (e.g., one or more individual providers and/or one or more individual practices). As further discussed below, it should be understood that terms may vary from provider to provider and the influence of organizations (e.g., organization 1002), practice groups (e.g., practice group 1004), and locations (e.g., location 1006) may vary greatly (e.g., in some embodiments, a provider may have great latitude in deciding what terms to use, where in another embodiment, a provider may have to follow strict standards set by an organization and/or practice group).

FIG. 10B depicts an exemplary chart 1050 displaying local term source entities (e.g., a particular provider, such as provider 1008) that each are part of a specific organization, part of a practice group, and of a particular location, a local term that is used by each provider, a source of a standard term corresponding to the local term (e.g., a standard term to which the local term may be normalized, as discussed previously herein), and the standard term.

As can be seen from FIG. 10B, row 1052 corresponds to exemplary provider D which is of location C, and part of (e.g., member of) practice group B and organization A. As shown in row 1052, provider D uses the local term "Heart Attack," which is normalized using the SNOMED-CT standard to the standard term "Myocardial Infarction." As shown in row 1054, provider C is of location B and also part of (e.g., member of) practice group B and organization A. Unlike provider D, in exemplary FIG. 10B, provider C uses local term "Heart Attack LV," which is also normalized using the SNOMED-CT standard to the standard term "Myocardial Infarction."

FIG. 10C in table 1070 provides examples of various domains (e.g., categories) and an exemplary corresponding applicable standard. For example, as shown in table 1070, the applicable standard for a "diagnosis" type term may be SNOMED-CT, while the applicable standard for an "immunization" type term may be CVX.

It should be understood that the embodiments shown if FIGS. 10A, 10B, and 10C are merely exemplary and not intended to be limiting. For example, categories or domains (as shown in FIG. 10C) may use any suitable applicable standard or standards and are not limited to the examples shown. Additionally, a provider (e.g., the provider 1008) may be part of any suitable hierarchy, or none at all.

Conclusion

As has been herein described, aspects of the present disclosure generally relate to systems and methods for accessing, managing, and exchanging patient information across a plurality of providers that may have various discrete medical record systems, including, but not limited to medical facilities, clinics, ambulatory emergency health systems, and other providers (e.g., heterogeneous healthcare providers).

In a particular embodiment, a Universal Medical Information System ("UMIS") allows various medical providers in various physical locations to securely store and exchange real-time data across discrete medical record systems. In one or more embodiments, the UMIS utilizes a substantially real-time bi-directional data exchange such that providers have the most up-to-date patient information available. Additionally, in some embodiments, the UMIS enables medical providers to exchange records and information according to their own terminology and format by normalizing, aggregating, and denormalizing data when a request for data is received. Instead of a complex mesh wherein, for example, a hospital has separate protocols and communications links in place for exchanging information with other hospitals and respective providers, who in turn have their own separate protocols and communications links in place for doing the same, the UMIS provides a streamlined, unified, universal system.

Systems and methods disclosed herein may be implemented in digital electronic circuitry, in computer hardware, firmware, software, or in combinations thereof. Apparatus of the claimed invention can be implemented in a computer program product tangibly embodied in a machine-readable storage device for execution by a programmable processor. Method steps according to the claimed invention can be performed by a programmable processor executing a program of instructions to perform functions of the claimed invention by operating based on input data, and by generating output data. The claimed invention may be implemented in one or several computer programs that are executable in a programmable system, which includes at least one programmable processor coupled to receive data from, and transmit data to, a storage system, at least one input device, and at least one output device, respectively. Computer programs may be implemented in a high-level or object-oriented programming language, and/or in assembly or machine code. The language or code can be a compiled or interpreted language or code. Processors may include general and special purpose microprocessors. A processor receives instructions and data from memories. Storage devices suitable for tangibly embodying computer program instructions and data include forms of non-volatile memory, including by way of example, semiconductor memory devices, such as EPROM, EEPROM, and flash memory devices; magnetic disks such as internal hard disks and removable disks; magneto-optical disks; and Compact Disk. Any of the foregoing can be supplemented by or incorporated in ASICs (application-specific integrated circuits).

The systems and methods described herein may be implemented on any suitable computing device and/or devices. Any reference to a processor, a server, or the like should be understood to mean one or more processors, one or more servers, etc., which may be in the same or various locations.

The foregoing description of the exemplary embodiments has been presented only for the purposes of illustration and description and is not intended to be exhaustive or to limit the inventions to the precise forms disclosed. Many modifications and variations are possible in light of the above teaching.

The embodiments were chosen and described in order to explain the principles of the inventions and their practical application so as to enable others skilled in the art to utilize the inventions and various embodiments and with various modifications as are suited to the particular use contemplated. Alternative embodiments will become apparent to those skilled in the art to which the present inventions pertain without departing from their spirit and scope. Accordingly, the scope of the present inventions is defined by the appended claims rather than the foregoing description and the exemplary embodiments described therein.

The invention claimed is:

1. A computer-implemented method for semantically normalizing patient data across siloed medical record systems via a mirrored database system, the method comprising the steps of:
    receiving a data request, by at least one processor, from a computer system associated with a particular user, to send data associated with a particular patient to the computer system;
    in response to receiving the data request from the computer system associated with the particular user:
        retrieving, by at least one processor, a first set of data associated with the particular patient from a local registry database operatively connected to a healthcare system database at a computer system of a particular healthcare provider, wherein the local registry database comprises a copy of health record data associated with the particular patient of the particular healthcare provider, the health record data originally stored at the healthcare system database and copied to the local registry database in response to the at least one processor receiving a notification of one or more locally initiated trigger events, and the first set of particular patient data includes one or more provider terms of the particular healthcare provider, and wherein the one or more locally initiated trigger events comprise a change in the health record data at the healthcare system database; and
        retrieving, by at least one processor, a set of local terms associated with the particular user from at least one central electronic database;
    normalizing, by at least one processor, the first set of particular patient data, wherein normalizing the first set of particular patient data comprises semantically converting at least one of the one or more provider terms to a first at least one generic term by matching a definition of the at least one of the one or more provider terms to a definition of the first at least one generic term;
    adding the normalized first set of particular patient data to a patient output record at the local registry database to preserve original health record data stored at the healthcare system database;
    denormalizing the patient output record, wherein denormalizing the patient output record comprises converting the at least one generic term to one or more local terms of a set of local terms associated with the particular user; and
    transmitting the denormalized patient output record to the computer system associated with the particular user, wherein the particular user receives the denormalized patient output record in real time via a display at the computer system, and wherein the denormalized patient output record is transmitted to the display via an internal routing engine at the computer system.

2. The computer-implemented method of claim 1, wherein normalizing the particular patient data further comprises:
    determining, by at least one processor, an applicable standard for normalizing the first set of particular patient data, wherein the applicable standard comprises a plurality of generic terms; and
    semantically converting, by at least one processor, at least one of the one or more provider terms to the first at least one generic term, wherein the at least one generic term is at least one generic term of the plurality of generic terms.

3. The computer-implemented method of claim 2, wherein semantically converting at least one of the one or more provider terms to the first at least one generic term comprises determining that the at least one generic term associated with the applicable standard is equivalent to the at least one provider term.

4. The computer-implemented method of claim 3, wherein semantically converting at least one of the one or more provider terms to the first at least one generic term further comprises:
    determining whether more than one generic term of the plurality of generic terms is equivalent to the at least one provider term; and
    based on determining that more than one generic term is equivalent to the at least one provider term, determining, based on a predetermined set of rules, to convert the at least one provider term to the at least one generic term.

5. The computer-implemented method of claim 4, further comprising the steps of:
    determining, by at least one processor, whether the particular user has permission to receive the first set of data; and
    at least partially in response to determining that the particular user has permission to receive the first set of data, adding, by at least one processor, the normalized first set of data to the patient output record.

6. The computer-implemented method of claim 5, wherein determining the particular user has permission to receive the first set of data is based on permissions selected from the group consisting of:
    provider-based privacy permissions;
    legal-based privacy permissions; and
    patient-based privacy permissions.

7. The computer-implemented method of claim 1, further comprising the steps of:
    retrieving, by at least one processor, a second set of data associated with the particular patient from a computer system associated with a second particular healthcare provider, wherein the second set of particular patient data includes one or more second provider terms used by the second particular healthcare provider;

normalizing, by at least one processor, the second set of particular patient data based on a predetermined set of rules, wherein normalizing the second set of particular patient data comprises converting at least one of the one or more second provider terms to a second at least one generic term; and adding the normalized second set of particular patient data to the patient output record.

8. The computer-implemented method of claim 7, wherein the predetermined set of rules correspond to the applicable standard for normalizing the first set of particular patient data.

9. The computer-implemented method of claim 1, wherein the one or more locally initiated trigger events further comprise a scheduled health record data retrieval event, an update to the particular patient's demographics, an update to the particular patient's prescriptions, or an update to the particular patient's appointment schedule.

10. A universal medical information system for managing patient records stored in various formats by heterogeneous health care systems via mirrored databases comprising:

at least one central electronic database for storing one or more patient health records;

a local registry database hosted by the universal medical archive system and operatively connected to a local archive associated with a third-party provider, the local archive comprising health record data associated with one or more patients of the third-party provider, wherein the local registry database comprises a copy of the health record data associated with the one or more patients of the third-party provider copied to the local registry database in response to the at least one processor receiving a notification of one or more locally initiated trigger events, and wherein the one or more locally initiated trigger events comprise a change to the health record data at the local archive; and at least one processor communicably coupled to the at least one central electronic database and the local registry database, wherein the at least one processor is configured to:

receive a set of local terms associated with a particular user; store, by at least one processor, the set of local terms in the at least one central electronic database;

receive a data request from a computer system associated with the particular user, to send data associated with a particular patient to the computer system;

in response to receiving the data request from the computer system associated with the particular user:

retrieve a first set of data associated with the particular patient from the copy of the health record data at the local registry database, wherein the first set of particular patient data includes one or more provider terms of the particular healthcare provider;

retrieve the set of local terms from the at least one central electronic database; and normalize the first set of particular patient data, wherein normalizing the first set of particular patient data comprises semantically converting at least one of the one or more provider terms to a first at least one generic term by matching a definition of the at least one of the one or more provider terms to a definition of the first at least one generic term;

add the normalized first set of particular patient data to a patient output record comprising the first at least one generic term at the local registry database thereby preserving original health record data stored at the local archive;

denormalize the patient output record, wherein denormalizing the patient output record comprises converting the first at least one generic term to one or more local terms of the set of local terms; and transmit the denormalized patient output record to the computer system associated with the particular user, wherein the particular user receives the denormalized patient output record in real time via a display at the computer system, and wherein the denormalized patient output record is transmitted to the display via an internal routing engine at the computer system.

11. The system of claim 10, wherein normalizing the particular patient data further comprises:

determining an applicable standard for normalizing the first set of particular patient data; and semantically converting at least one of the one or more provider terms to the first at least one generic term, wherein the at least one generic term is a term associated with the applicable standard.

12. The system of claim 11, wherein semantically converting at least one of the one or more provider terms to the first at least one generic term comprises determining that the at least one generic term associated with the applicable standard is equivalent to the at least one provider term.

13. The system of claim 12, wherein semantically converting at least one of the one or more provider terms to the first at least one generic term further comprises:

determining whether more than one generic term is equivalent to the at least one provider term; and based on determining that more than one generic term is equivalent to the at least one provider term, determining which generic term to convert the at least one provider term to, based on a predetermined set of rules.

14. The system of claim 13, wherein the at least one processor is further configured to:

determine whether the particular user has permission to receive the first set of data; and at least partially in response to determining that the particular user has permission to receive the first set of data, add the normalized first set of data to the patient output record.

15. The system of claim 14, wherein determining the particular user has permission to receive the first set of data is based on permissions selected for the group consisting of:

provider-based privacy permissions;

legal-based privacy permissions; and patient-based privacy permissions.

16. The system of claim 10, wherein the at least one processor is further configured to:

retrieve a second set of data associated with the particular patient from a computer system associated with a second particular healthcare provider, wherein the second set of particular patient data includes one or more second provider terms used by the second particular healthcare provider;

normalize the second set of particular patient data based on the predetermined set of rules, wherein normalizing the second set of particular patient data comprises converting at least one of the one or more second provider terms to a second at least one generic term; and add the normalized second set of particular patient data to the patient output record.

17. The universal medical information system of claim 10, wherein the one or more locally initiated trigger events further comprise a scheduled health record data retrieval event, an update to the one or more patients' demographics, an update to the one or more patients' prescriptions, or an update to the one or more patients' appointment schedules.

18. A universal medical information system for managing patient records stored in various formats by heterogeneous health care systems via mirrored databases comprising:
    at least one central electronic database for storing one or more patient health records;
    a local registry database hosted by the universal medical archive system and operatively connected to a local archive associated with a third-party provider, the local archive comprising health record data associated with the one or more patients of the third-party provider, wherein the local registry database comprises a copy of the health record data associated with the one or more patients of the third-party provider copied to the local registry database in response to the at least one processor receiving a notification of one or more locally initiated trigger events, and wherein the one or more locally initiated trigger events comprise a change in the health record data at the local archive; and
    at least one processor communicably coupled to the at least one central electronic database and the local registry database, wherein the at least one processor is configured to:
        receive a data request from a computer system associated with a particular user to send data associated with a particular patient to the computer system;
        in response to receiving the data request from the computer system associated with the particular user:
            retrieve a plurality of data sets associated with the particular patient from the local registry database, wherein the plurality of data sets are copies of data sets stored at the local archive and include a plurality of provider terms;
        determining an applicable standard for each of the plurality of data sets; and
            semantically converting one or more provider terms of the plurality of provider terms to one or more generic terms by matching a definition of the one or more provider terms to a definition of the one or more generic terms;
            add each of the plurality of data sets to a patient output record at the local registry database thereby preserving original health record data stored at the local archive;
            determine whether the patient output record includes one or more duplicate generic terms;
            in response to determining that the patient output record includes one or more duplicate generic terms, modify the patient output record to exclude the one or more duplicate generic terms;
            converting each of the one or more generic terms to one or more local terms, wherein the one or more local terms are terms associated with the particular user; and
            transmit the patient output record to the computer system associated with the particular user, wherein the particular user receives the patient output record in real time via a display at the computer system, and wherein the patient output record is transmitted to the display via an internal routing engine at the computing system.

19. The universal medical information system of claim 18, wherein the one or more locally initiated trigger events further comprise a scheduled health record data retrieval event, an update to the one or more patients' demographics, an update to the one or more patients' prescriptions, or an update to the one or more patients' appointment schedules.

20. A computer-implemented method for managing patient data stored in various formats at siloed medical record locations comprising the steps of:
    receiving a request from a healthcare provider to provide particular data associated with a particular patient, wherein the request comprises a local set of rules for naming and formatting patient data;
    in response to receiving the request from the provider, extracting a data element corresponding to the particular data from a plurality of data elements, wherein the plurality of data elements are formatted according to a centralized set of rules, include a source identifier, and are stored in a local registry database, wherein the local registry database comprises a copy of health record data associated with the particular patient originally stored at a local archive and copied to the local registry database in response to the at least one processor receiving a notification of one or more locally initiated trigger events, wherein the one or more locally initiated trigger events comprise a change in the health record data at the local archive, and wherein the local archive is a part of a separate healthcare records system;
    determining whether the source identifier of the extracted data element corresponds to the healthcare provider;
    in response to determining that the source identifier of the extracted data element does not correspond to the healthcare provider, determining whether the extracted data is named and formatted according to the local set of rules;
    in response to determining that the extracted data is not named and formatted according to the local set of rules, semantically conforming the extracted data with the local set of rules; and
    transmitting the conformed extracted data to the healthcare provider, wherein a user at the healthcare provider receives the conformed extracted data in real time via a computing device display at the healthcare provider, and wherein the conformed extracted data is transmitted to the display via an internal routing engine at the healthcare provider.

* * * * *